United States Patent [19]
Kohl et al.

[11] Patent Number: 6,162,809
[45] Date of Patent: Dec. 19, 2000

[54] PYRIDYLTHIO COMPOUNDS FOR CONTROLLING HELICOBACTER BACTERIA

[75] Inventors: Bernhard Kohl; Gerhard Grundler; Jörg Senn-Bilfinger, all of Constance, Germany

[73] Assignee: Byk Gulden Lomberg Chemische Fabrik GmbH, Constance, Germany

[21] Appl. No.: 08/776,047

[22] PCT Filed: Jul. 19, 1995

[86] PCT No.: PCT/EP95/02851

§ 371 Date: Jan. 17, 1995

§ 102(e) Date: Jan. 17, 1997

[87] PCT Pub. No.: WO96/02505

PCT Pub. Date: Feb. 1, 1996

[30] Foreign Application Priority Data

Jul. 10, 1994 [CH] Switzerland .............................. 2303/94

[51] Int. Cl.[7] ...................... A61K 31/444; A61K 31/506; C07D 401/12; C07D 403/12
[52] U.S. Cl. ............... 514/274; 514/252.14; 514/253.01; 514/269; 514/308; 514/333; 514/335; 544/298; 544/316; 544/319; 544/295; 546/148; 546/256; 546/261
[58] Field of Search ...................... 514/336, 337, 514/338, 339, 342, 269, 274, 333, 335; 546/193, 194, 256, 261; 544/298, 316, 319

[56] References Cited

FOREIGN PATENT DOCUMENTS

WO 94/13290  6/1994  WIPO .

OTHER PUBLICATIONS

Ota et al., Chemical Abstracts, vol. 108, abstract 186590u, 1988.

*Primary Examiner*—Richard L. Raymond
*Attorney, Agent, or Firm*—Jacobson, Price, Holman & Stern, PLLC

[57] ABSTRACT

Pyridinylthiomethyl- and pyrimidinylthiomethyl-pyridines and their pharmacologically-acceptable compositions are useful for controlling Helicobacter bacteria and for treating those afflicted with diseases based on Helicobacter bacteria.

20 Claims, No Drawings

PYRIDYLTHIO COMPOUNDS FOR CONTROLLING HELICOBACTER BACTERIA

This application is a 371 of PCT/EP95/02851, filed Jul. 19, 1995.

FIELD OF APPLICATION OF THE INVENTION

The invention relates to compounds which are intended to be used in the pharmaceutical industry as active compounds for the production of medicaments.

DESCRIPTION OF THE INVENTION

The invention relates to compounds of the formula I (see attached formula sheet), in which R is hydrogen, 1–4C-alkyl, halogen, trifluoromethyl, 1–4C-alkoxycarbonyl, carboxyl or cyano, R1 is hydrogen or 1–4C-alkyl, R2 is hydrogen or 1–4C-alkyl, R3 is hydrogen, 1–4C-alkyl, 1–4C-alkoxy or halogen, R4 is a mono- or di-1–4C-alkylcarbamoyl or -thiocarbamoyl radical, an N-1–4C-alkyl-N'-cyanoamidino radical, a 1-N-1–4C-alkylamino-2-nitroethylene radical, an N-2-propynyl-N'-cyanoamidino radical, an aminosulfonylamidino radical, the radical —N(R7)R8 or an R9- and R10-substituted cyclic system or bicyclic system which is selected from the group consisting of benzene, naphthalene, furan, thiophene, pyrrole, oxazole, isoxazole, thiazole, thiazoline, isothiazole, imidazole, imidazoline, pyrazole, triazole, tetrazole, thiadiazole, thiadiazole-i-oxide, oxadiazole, pyridine, pyridine-N-oxide, pyrimidine, triazine, pyridone, benzimidazole, imidazopyridine, benzothiazole, benzoxazole and quinoline, R5 is hydrogen, 1–4C-alkyl, 1–4C-alkoxy or halogen, R6 is hydrogen or 1–4C-alkyl, R7 is 1–7C-alkyl, 3–7C-cycloalkyl or Ar-1–4C-alkyl and R8 is 1–7C-alkyl, 3–7C-cycloalkyl or Ar-1–4C-alkyl, where Ar is phenyl, furyl, naphthyl, tetrahydronaphthyl or R11-, R12- and R13-substituted phenyl, or in which R7 and R8 together, and including the nitrogen atom to which both are bonded, are an unsubstituted or substituted 5- or 6-membered ring hetero(bi)cyclic system, which is selected from the group consisting of piperidine, piperazine, morpholine, indoline, 1,2,3,4-tetrahydroquinoline and 1,2,3,4-tetrahydroisoquinoline, where a substituted piperidino radical is substituted by one, two or three identical or different substituents selected from the group consisting of 1–4C-alkyl, 1–4C-alkoxycarbonyl, hydroxy -1–4C-alkyl, phenyl, R11-, R12- and R13-substituted phenyl, phenyl-1–4C-alkyl, benzoyl, halogen-substituted benzoyl and carboxyl, a substituted piperazino radical can be substituted in the 2-, 3-, 5- or 6-position by a 1–4C-alkyl radical and is substituted in the 4-position by a substituent selected from the group consisting of 1–4C-alkyl, 3–7C-cycloalkyl, 3–7C-cycloalkyl-1–4C-alkyl, 1–4C-alkoxycarbonyl-1–4C-alkyl, carbamoyl, —$C_pH_{(2p-2)}$—R14 and —$C_qH_{2q}$—R14, a substituted morpholino radical is substituted by one or two identical or different 1–4C-alkyl radicals, a substituted indolin-1-yl radical can be substituted in the 2- and/or 3-position by a carboxyl group or by one or two identical or different 1–4C-alkyl radicals, and can be substituted in the benzo moiety by one or two identical or different substituents selected from the group consisting of 1–4C-alkyl, halogen and nitro, a substituted 1,2,3,4-tetrahydroquinoline radical is substituted by one or two identical or different substituents selected from the group consisting of 1–4C-alkyl and halogen, a substituted 1,2,3,4-tetrahydroisoquinoline radical is substituted by one or two identical or different substituents selected from the group consisting of 1–4C-alkyl, carboxyl and phenyl, R9 is hydrogen, 1–4C-alkyl, hydroxyl, 1–4C-alkoxy, halogen, nitro, guanidino, carboxyl, 1–4C-alkoxycarbonyl, R15-substituted 1–4C-alkyl or —N(R16)R17, R10 is hydrogen, 1–4C-alkyl, hydroxyl, 1–4C-alkoxy, halogen or trifluoromethyl, R11 is hydrogen, 1–4C-alkyl, hydroxyl, 1–4C-alkoxy, 1–4C-alkylcarbonyl, halogen, 1–4C-alkylamino or nitro, R12 is hydrogen, 1–4C-alkyl, hydroxyl, 1–4C-alkoxy, halogen or nitro, and R13 is hydrogen or trifluoromethyl, R14 is an R9- and R10-substituted cyclic system or bicyclic system which is selected from the group consisting of benzene, naphthalene, furan, thiophene, pyrrole, oxazole, isoxazole, thiazole, thiazoline, isothiazole, imidazole, imidazoline, pyrazole, triazole, tetrazole, thiadiazole, oxadiazole, pyridine, pyridine-N-oxide, pyrimidine, benzimidazole and quinoline, R15 is hydroxyl, 1–4C-alkoxy, carboxyl, 1–4C-alkoxycarbonyl or —N(R16)R17, where R16 is hydrogen, 1–4C-alkyl or —CO—R18 and R17 is hydrogen or 1–4C-alkyl, or where R16 and R17, together and including the nitrogen atom to which both are bonded, are a piperidino or morpholino radical, R18 is hydrogen, 1–4C-alkyl or 1–4C-alkoxy, W is CH or N, X is O (oxygen), N-1–4C-alkyl or S, Y is O (oxygen), N-1–4C-alkyl, S, SO or $SO_2$, Z is O (oxygen), N-1–4C-alkyl, S, SO or $SO_2$, m is a number from 1 to 7, n is the number 0, 1 or 2, r is a number from 2 to 4, t is the number 0 or 1, u is a number from 0 to 4, v is the number 0 or 1, p is a number from 2 to 4 and q is a number from 0 to 4 and their salts, where t and/or v are not the number 1 if m is the number 1,

Z is not SO or $SO_2$ if u is the number 0, and where

R4 is not —N(R7)R8 or an N (nitrogen)-bonded cyclic system or bicyclic system if Z is O, S, SO or $SO_2$, v is the number 1 and u is the number 0.

1–4C-Alkyl represents straight-chain or branched alkyl radicals having 1 to 4 carbon atoms.

Examples which may be mentioned are the butyl, iso-butyl, sec-butyl, tert-butyl, propyl, isopropyl, ethyl and methyl radicals.

Halogen within the meaning of the present invention is bromine, chlorine or fluorine.

1–4C-Alkoxy represents a radical which, beside the oxygen atom, contains one of the abovementioned 1–4C-alkyl radicals. Examples which may be mentioned are the methoxy and the ethoxy radicals.

1–4C-Alkoxycarbonyl represents a radical which, beside the carbonyl group, contains one of the abovementioned 1–4C-alkoxy radicals. Examples which may be mentioned are the methoxycarbonyl and the ethoxycarbonyl radicals.

Mono- or di-1–4C-alkylcarbamoyl radicals are carbamoyl radicals (—CO—NH$_2$) which are substituted by one or two radicals which are identical to or different from the abovementioned 1–4C-alkyl radicals. Examples which may be mentioned are the methylcarbamoyl, the isopropylcarbamoyl and the dimethylcarbamoyl radicals.

Mono- or di-1–4C-alkylthiocarbamoyl radicals are thiocarbamoyl radicals (—CS—NH$_2$) which are substituted by one or two radicals which are identical to or different from the abovementioned 1–4C-alkyl radicals. Examples which may be mentioned are the methylthiocarbamoyl, the isopropylthiocarbamoyl and the dimethylthiocarbamoyl radicals.

An N-1–4C-alkyl-N'-cyanoamidino radical which may be mentioned, for example, is in particular the N-methyl-N'-cyanoamidino radical [—C(=NCN)—NH—CH$_3$].

A 1-N-1–4C-alkylamino-2-nitroethylene radical which may be mentioned, for example, is in particular the 1-N-methylamino-2-nitroethylene radical [—C(NHCH$_3$)=CHNO$_2$], where the radicals —NHCH$_3$ and —NO$_2$ can be in the cis or trans position relative to one another.

1–7C-Alkyl represents straight-chain or branched alkyl radicals having 1 to 7 carbon atoms. Examples which may be mentioned are the heptyl, isoheptyl(2-methylhexyl), hexyl, isohexyl(2-methylpentyl), neohexyl(2,2-dimethylbutyl), pentyl, isopentyl(3-methylbutyl), neopentyl (2,2-dimethylpropyl), butyl, isobutyl, sec-butyl, tert-butyl, propyl, isopropyl, ethyl and methyl radicals.

3–7C-Cycloalkyl represents cycloalkyl radicals having 3 to 7 carbon atoms, i.e. the cyclopropyl, the cyclobutyl, the cyclopentyl, the cyclohexyl and the cycloheptyl radicals.

Ar-1–4C-alkyl represents one of the abovementioned Ar-substituted 1–4C-alkyl radicals. Examples which may be mentioned are the phenethyl, the benzyl, the 2-furylmethyl (=furfuryl) and the 1-naphthylmethyl radicals.

Hydroxy-1–4C-alkyl represents one of the abovementioned 1–4C-alkyl radicals which is substituted by hydroxyl. Examples which may be mentioned are the hydroxymethyl radical, the 2-hydroxyethyl radical or the 3-hydroxypropyl radical.

3–7C-Cycloalkyl-1–4C-alkyl represents one of the abovementioned 1–4C-alkyl radicals which is substituted by one of the abovementioned 3–7C-cycloalkyl radicals. Examples which may be mentioned are the cyclopropylmethyl, the cyclohexylmethyl and the cyclohexylethyl radicals.

1–4C-Alkoxycarbonyl-1–4C-alkyl represents one of the abovementioned 1–4C-alkyl radicals which is substituted by one of the abovementioned 1–4C-alkoxycarbonyl radicals. An example which may be mentioned is the ethoxycarbonylmethyl radical.

Exemplary R15-substituted 1–4C-alkyl radicals which may be mentioned are the 2-methoxycarbonylethyl, the 2-ethoxycarbonylethyl, the methoxycarbonylmethyl, the carboxymethyl, the 2-hydroxyethyl, the methoxymethyl, the 2-methoxyethyl, the dimethylaminomethyl and the 2-dimethylaminoethyl radicals.

1–4C-alkylcarbonyl represents a radical which, beside the carbonyl group, contains one of the abovementioned 1–4C-alkyl radicals. An example which may be mentioned is the acetyl radical.

Possible radicals —C$_m$H$_{2m}$—, —C$_r$H$_{2r}$—, —C$_u$H$_{2u}$— and —C$_q$H$_{2q}$— are straight-chain or branched radicals. Examples which may be mentioned are the heptylene, isoheptylene (2-methylhexylene), hexylene, isohexylene (2-methylpentylene), neohexylene (2,2-dimethylbutylene), pentylene, isopentylene (3-methylbutylene), neopentylene (2,2-dimethylpropylene), butylene, isobutylene, sec-butylene, tert-butylene, propylene, isopropylene, ethylene and methylene radicals.

Radicals —C$_m$H$_{2m}$— which are preferably to be mentioned are the ethylene (—CH$_2$CH$_2$—), the butylene (—CH$_2$CH$_2$CH$_2$CH$_2$—) and in particular the propylene (—CH$_2$CH$_2$CH$_2$—) radicals.

A radical —C$_r$H$_{2r}$— which is preferably to be mentioned is the methylene radical or, in a further preferred embodiment, r is the number 0, so that the expression C$_r$H$_{2r}$ disappears or is a bonding dash.

In a further preferred embodiment, u is the number 0, so that the expression C$_u$H$_{2u}$ disappears or is a bonding dash and the radical R4 is bonded directly to the group Z.

In one embodiment, t is the number 1.

In a further embodiment, t is the number 0, so that the expression [Y—C$_r$H$_{2r}$]$_t$ disappears or is a bonding dash.

In a further preferred embodiment, v is the number 0, so that the expression [Z—C$_u$H$_{2u}$] disappears or is a bonding dash.

Radicals —C$_p$H$_{(2p-2)}$— which may be mentioned are the vinylene, the 2-butenylene, the 3-butenylene and in particular the 1-propenylene and the 2-propenylene radicals.

A radical —C$_q$H$_{2q}$— which is preferably to be mentioned is the methylene radical or, in a further preferred embodiment, q is the number 0, so that the expression C$_q$H$_{2q}$ disappears or is a bonding dash.

The substituents R9 and R10 can be bonded to the cyclic systems or bicyclic systems R4 in any conceivable position. Exemplary R9- and R10-substituted radicals R4 which may be mentioned are: 4-methylphenyl, 3-dimethylaminomethylphenyl, 3-piperidinomethylphenyl, 3-carboxymethylphenyl, 2-dimethylaminomethyl-5-methyl-3-furyl, 1-methylpyrrole-3-yl, 4,5-dimethyloxazol-2-yl, 3,5-dimethylisoxazol-4-yl, 4,5-dimethylthiazol-2-yl, 4-methyl-5-carboxymethylthiazol-2-yl, 1-methylimidazol-2-yl, 1-methylpyrazol-3-yl, 1-(2-dimethylaminoethyl)pyrazol-3-yl, 5-methyl-1,3,4-oxadiazol-2-yl, 1-methyl-1,2,3-triazol-4-yl, 1-methyl-1,2,4-triazol-3-yl, 1-(2-dimethylaminoethyl)-1, 2,3-triazol-4-yl, 1-methyl-tetrazol-5-yl, 1-(2-dimethylaminoethyl)tetrazol-5-yl, 1-carboxymethyltetrazol-5-yl, 5-methyl-1,3,4-thiadiazol-2-yl, 5-trifluoromethyl-1,3,4-thiadiazol-2-yl, 1-(2-hydroxyethyl)tetrazol-5-yl, 2-amino-1,3,4-thiadiazol-2-yl, 3-amino-1,2,4-triazol-5-yl, 4-methyl-5-trifluoromethyl-1,2,4-triazol-3-yl, 4-aminopyrimidin-2-yl, 3-methyl-2-furyl, 2-methyl-3-furyl, 5-methyl-2-furyl, 5-ethyl-2-furyl, 3-methoxy-2-furyl, 5-dimethylaminomethyl-2-furyl, 5-N-morpholinomethyl-2-furyl, 5-methoxymethyl-2-furyl, 5-hydroxymethyl-2-furyl, 5-N-piperidinomethyl-2-furyl, 5-chloro-2-furyl, 5-fluoro-2-furyl, 5-methyl-2-thienyl, 5-chloro-2-thienyl, 3-methyl-2-thienyl, 3-amino-2-thienyl, 3-guanidino-2-thienyl, 3-methoxy-2-thienyl, 2-methyl-3-thienyl, 5-dimethylaminomethyl-2-thienyl, 5-N-morpholinomethyl-2-thienyl, 5-methyl-2-pyrroleyl, 2,5-dimethyl-1-pyrroleyl, 1,5-dimethyl-2-pyrroleyl, 1-methyl-2-pyrroleyl, 2-amino-4-thiazolyl, 2-methyl-4-thiazolyl, 2-amino-5-methyl-4- thiazolyl, 4-methyl-5-thiazolyl, 2-dimethylaminomethyl-4-thiazolyl, 2-guanidino-4-thiazolyl, 2-formylamino-4-thiazolyl, 2-N-morpholinomethyl-4-thiazolyl, 4-methyl-5-oxazolyl, 3-guanidino-1-pyrazolyl, 3-guanidino-4-pyrazolyl, 2-methyl-4-imidazolyl, 5-methyl-4-imidazolyl, 2-methyl-1-imidazolyl, 2-methyl-5-nitro-1-imidazolyl, 4,5-dimethyl-2-imidazolyl, 4-hydroxymethyl-5-methyl-1-imidazolyl, 3-methyl-1-pyrazolyl, 5-amino-1,2,4-thiadiazol-3-yl, 4-methoxy-2-pyridinyl, 4-methoxy-3-methyl-2-pyridinyl and 3,4-dimethoxypyridinyl.

Exemplary R11-, R12- and R13-substituted phenyl radicals which may be mentioned are the radicals 3,4-dihydroxy-, 3-hydroxy-4-methoxy-, 3,4-dimethoxy-, 2-methoxy-, 2-ethoxy-, 3-methoxy-, 4-methoxy-, 2-hydroxy-, 3-hydroxy-, 4-hydroxy-, 3,4-dihydroxy-, 4-acetyl-, 4-fluoro-, 4-chloro-, 2-chloro-, 3-chloro-, 3,4-dichloro-, 3-trifluoromethyl-, 2-trifluoromethyl-, 2-methyl-, 3-methyl-, 4-methyl-, 2,3-dimethyl-, 2,4-dimethyl-, 3,4-dimethyl-, 2,5-dimethyl-, 4-nitro-, 2,6-dinitro-4-trifluoromethyl- and 5-chloro-2-methylaminophenyl.

Substituted piperidino radicals which may be mentioned are, for example, the 2-carboxypiperidino, 2-n-propylpiperidino, 5-ethyl-2-methylpiperidino, 4-hydroxymethyl-4-phenylpiperidino, 4-n-propylpiperidino, 4-(3-phenylpropyl)piperidino, 2,6-dimethylpiperidino, 4-phenyl-4-propyloxycarbonyl-piperidino, 4-ethoxycarbonyl-4-phenylpiperidino, 4-carboxy-4-phenylpiperidino, 4-carboxypiperidino, 4-(4-fluorobenzoyl)piperidino, 4-(4-chlorobenzoyl)-piperidino, 2,3-dicarboxypiperidino, 2,4-dicarboxy-piperidino, 2,6-dicarboxypiperidino, 2-ethoxycarbonyl-piperidino, 2-methylpiperidino, 2,6-dimethylpiperidino, 2-hydroxymethylpiperidino, 2-ethylpiperidino, 2-(2-hydroxyethyl)piperidino, 3-ethoxycarbonylpiper-idino and the 4-benzylpiperidino radicals.

Substituted piperazino radicals which may be mentioned are, for example, the 4-methylpiperazino, 4-phenylpiperazino, 4-(2-methylphenyl)piperazino, 4-(2,3-dimethylphenyl)piperazino, 4-(2-chlorophenyl)piperazino, 4-(2-methoxyphenyl)piperazino, 4-(2-ethoxyphenyl) piperazino, 4-(3-chlorophenyl)piperazino, 4-(4-fluorophenyl)piperazino, 4-(4-chlorophenyl)piperazino, 4-(4-methoxyphenyl)piperazino, 4-carbamoylpiperazino, 3-methyl-4-(4-chlorophenyl)piperazino, 3-methyl-4-(4-methoxyphenyl)piperazino, 3-methyl-4-(4-methylphenyl) piperazino, 4-(2,4-dimethylphenyl)piperazino, 4-(3,4-dichlorophenyl)piperazino, 4-(3,4-dimethylphenyl) piperazino, 3-methyl-4-phenylpiperazino, 3-methyl-4-(3-chlorophenyl)-piperazino, 4-benzylpiperazino, 4-propylpiperazino, 4-(3-methylphenyl)piperazino, 4-(3-methoxyphenyl)-piperazino, 4-(4-methylphenyl)piperazino, 4-(2,5-dimethylphenyl)piperazino, 4-cyclopropylpiperazino, 4-cyclobutylpiperazino, 4-cyclopentylpiperazino, 4-cyclohexylpiperazino, 4-cycloheptylpiperazino, 4-n-butylpiperazino, 4-iso-butylpiperazino, 4-tert-butylpiperazino, 4-(1-phenylethyl) piperazino, 4-ethoxycarbonylmethylpiperazino, 4-(2-phenylethyl)-piperazino, 4-(2-cyclohexylethyl)piperazino, 4-(2-hydroxy-phenyl)piperazino, 4-(3,4-dimethoxyphenyl) piperazino, 4-isopropylpiperazino, 3-methyl-4-(3-methoxyphenyl)-piperazino, 4-(4-hydroxyphenyl) piperazino, 3-methyl-4-(3-methylphenyl)piperazino, 4-(3-hydroxyphenyl)-piperazino, 4-(2,6-dinitro-4-trifluoromethylphenyl)-piperazino, 4-(4-nitrophenyl) piperazino, 4-(4-acetyl-phenyl)piperazino, 4-(2-chloro-5-thienylmethyl)piper-azino and the 4-[2-(2-methyl-5-nitro-1-imidazolyl)ethyl]piperazino radicals.

A substituted morpholino radical which may be mentioned is, for example, the 3,5-dimethylmorpholino radical.

Substituted indolin-1-yl radicals which may be mentioned are, for example, the 2-carboxy-1-indolinyl, 6-fluoro-1-indolinyl, 5-bromo-1-indolinyl, 2,7-dimethyl-1-indolinyl, 2-methyl-1-indolinyl, 5-bromo-7-nitro-1-indolinyl, 5-nitro-1-indolinyl, 2,3-dimethyl-1-indolinyl and the 6-nitro-1-indolinyl radicals.

Substituted 1,2,3,4-tetrahydroquinoline radicals which may be mentioned are, for example, the 2-ethoxycarbonyl-1,2,3,4-tetrahydro-1-quinolinyl, 2-methyl-1,2,3,4-tetrahydro-1-quinolinyl, 6-methyl-1,2,3,4-tetrahydro-1-quinolinyl, 6-fluoro-2-methyl-1,2,3,4-tetrahydro-1-quinolinyl, 4-methyl-1,2,3,4-tetrahydro-1-quinolinyl and the 2-fluoro-6-methyl-1,2,3,4-tetrahydro-1-quinolinyl radicals.

A substituted 1,2,3,4-tetrahydroisoquinoline radical which may be mentioned is, for example, the 3-carboxy-1,2,3,4-tetrahydro-2-isoquinolinyl radical.

Suitable salts of compounds of the formula I in which n is the number 0 are all acid addition salts. Particular mention may be made of the pharmacologically tolerable salts of the inorganic and organic acids customarily used in pharmacy. Pharmacologically non-tolerable salts which, for example, can be initially obtained as process products in the preparation of the compounds according to the invention on the industrial scale, and converted into pharmacologically tolerable salts by processes known to the person skilled in the art. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether it is a mono- or polybasic acid and depending on which salt is desired—in an equimolar quantitative ratio or one differing therefrom.

For compounds of the formula I in which n is the numbers 1 or 2, and/or for compounds with a carboxyl group suitable salts are also salts with bases. Examples of basic salts which may be mentioned are lithium, sodium, potassium, calcium, aluminum, magnesium, titanium, ammonium, meglumine or guanidinium salts, here too in salt preparation the bases being employed in an equimolar quantitative ratio or one differing therefrom.

Compounds to be emphasized are those of the formula I in which

R is hydrogen, 1–4C-alkyl or halogen,

R1 is hydrogen,

R2 is hydrogen or 1–4C-alkyl,

R3 is hydrogen, 1–4C-alkyl, 1–4C-alkoxy or halogen,

R4 is a mono- or di-1–4C-alkylthiocarbamoyl radical, the radical —N(R7)R8 or an R9- and R10-substituted cyclic system or bicyclic system which is selected from the group consisting of benzene, naphthalene, furan, thiophene, pyrrole, oxazole, isoxazole, thiazole, thiazoline, isothiazole, imidazole, imidazoline, pyrazole, triazole, tetrazole, thiadiazole, thiadiazole-1-oxide, oxadiazole, pyridine, pyridine-N-oxide, pyrimidine, triazine, pyridone, benzimidazole, imidazopyridine, benzothiazole, benzoxazole and quinoline, R5 is hydrogen or 1–4C-alkyl,
R6 is hydrogen or 1–4C-alkyl,
R7 is 1–7C-alkyl and
R8 is Ar-1–4C-alkyl, where
Ar is phenyl, furyl, naphthyl, tetrahydronaphthyl or R11-, R12- and R13-substituted phenyl, or in which
R7 and R8, together and including the nitrogen atom to which both are bonded, are an unsubstituted or substituted 5- or 6-membered ring hetero(bi)cyclic system which is selected from the group consisting of piperidine, piperazine, 1,2,3,4-tetrahydroquinoline and 1,2,3,4-tetrahydroisoquinoline, where
    a substituted piperidino radical is substituted by one, two or three identical or different substituents selected from the group consisting of 1–4C-alkyl, phenyl, R11-, R12- and R13-substituted phenyl and phenyl-1–4C-alkyl,
    a substituted piperazino radical in the 4-position is substituted by a substituent selected from the group consisting of 1–4C-alkyl, 1–4C-alkoxycarbonyl-1–4C-alkyl, —$C_pH_{(2p-2)}$—R14 and —$C_qH_{2q}$—R14,
    a substituted 1,2,3,4-tetrahydroquinoline radical is substituted by one or two identical or different substituents selected from the group consisting of 1–4C-alkyl and halogen,
    a substituted 1,2,3,4-tetrahydroisoquinoline radical is substituted by one or two identical or different substituents selected from the group consisting of 1–4C-alkyl, carboxyl and phenyl,
R9 is hydrogen, 1–4C-alkyl, halogen, nitro, carboxyl, 1–4C-alkoxycarbonyl or R15-substituted 1–4C-alkyl,
R10 is hydrogen or 1–4C-alkyl,
R11 is hydrogen, 1–4C-alkyl, hydroxyl, 1–4C-alkoxy, halogen or nitro,
R12 is hydrogen, 1–4C-alkyl, hydroxyl or 1–4C-alkoxy and
R13 is hydrogen,
R14 is an R9- and R10-substituted cyclic system or bicyclic system which is selected from the group consisting of benzene, naphthalene, furan, thiophene, pyrrole, oxazole, isoxazole, thiazole, thiazoline, isothiazole, imidazole, imidazoline, pyrazole, triazole, tetrazole, thiadiazole, oxadiazole, pyridine, pyridine-N-oxide, pyrimidine, benzimidazole and quinoline,
R15 is carboxyl, 1–4C-alkoxycarbonyl or —N(R16)R17, where
R16 is hydrogen or 1–4C-alkyl and
R17 is 1–4C-alkyl, or where
R16 and R17, together and including the nitrogen atom to which both are bonded, are a piperidino or morpholino radical,
W is CH or N,
X is O (oxygen), N-1–4C-alkyl or S,
Z is O (oxygen), N-1–4C-alkyl, S or $SO_2$,
m is a number from 1 to 6,
n is the number 0,
t is the number 0,
u is a number from 0 to 4,
v is the number 0 or 1,
p is a number from 2 to 4 and
q is a number from 0 to 2
and their salts, where v is not the number 1 if m is the number 1,
Z is not $SO_2$ if u is the number 0, and where
R4 is not —N(R7)R8 or an N (nitrogen)-bonded cyclic system or bicyclic system if Z is O, S or $SO_2$, v is the number 1 and u is the number 0.

Compounds particularly to be emphasized are those of the formula I, in which
R is hydrogen or 1–4C-alkyl,
R1 is hydrogen,
R2 is hydrogen,
R3 is hydrogen, 1–4C-alkyl, 1–4C-alkoxy or halogen,
R4 is a mono- or di-1–4C-alkylthiocarbamoyl radical, the radical —N(R7)R8 or an R9- and R10-substituted cyclic system or bicyclic system which is selected from the group consisting of benzene, furan, thiophene, thiazole, isothiazole, imidazole, triazole, tetrazole, thiadiazole, pyridine, pyrimidine, benzimidazole and quinoline,
R5 is hydrogen
R6 is hydrogen or 1–4C-alkyl,
R7 is 1–7C-alkyl and
R8 is Ar-1–4C-alkyl, where
Ar is phenyl, or in which
R7 and R8, together and including the nitrogen atom to which both are bonded, are an unsubstituted or substituted 5- or 6-membered ring hetero(bi)cyclic system which is selected from the group consisting of piperidine, piperazine and 1,2,3,4-tetrahydroisoquinoline, where
    a substituted piperidino radical is substituted by one, two or three identical or different substituents selected from the group consisting of 1–4C-alkyl, phenyl and phenyl-1–4C-alkyl,
    a substituted piperazino radical is substituted in the 4-position by a substituent selected from the group consisting of 1–4C-alkyl, 1–4C-alkoxycarbonyl-1–4C-alkyl, —$C_pH_{(2p-2)}$—R14 and —$C_qH_{2q}$—R14,
    a substituted 1,2,3,4-tetrahydroisoquinoline radical is substituted by one or two identical or different substituents selected from the group consisting of 1–4C-alkyl and carboxyl,
R9 is hydrogen, 1–4C-alkyl, halogen, nitro, carboxyl, 1–4C-alkoxycarbonyl or R15-substituted 1–4C-alkyl,
R10 is hydrogen or 1–4C-alkyl,
R14 is an R9- and R10-substituted cyclic system or bicyclic system which is selected from the group consisting of benzene, furan, thiophene, thiazole, isothiazole, imidazole, triazole, tetrazole, thiadiazole, pyridine, pyrimidine, benzimidazole and quinoline,
R15 is carboxyl, 1–4C-alkoxycarbonyl or —N(R16)R17, where
R16 is 1–4C-alkyl and
R17 is 1–4C-alkyl, or where
R16 and R17, together and including the nitrogen atom to which both are bonded, are a piperidino or morpholino radical,
W is CH or N,
X is S,
z is S,
m is a number from 1 to 5,
n is the number 0,
t is the number 0, u is a number from 0 to 2, v is the number 0 or 1, p is a number from 2 to 4 and q is a number from 0 to 2 and their salts, where v is not the number 1 if m is the number 1, and where

R4 is not —N(R7)R8 or an N (nitrogen)-bonded cyclic system or bicyclic system if Z is S, v is the number 1 and u is the number 0.

Exemplary compounds are those of the formula I, in which

R is hydrogen,

R1 is hydrogen,

R2 is hydrogen,

R3 is hydrogen, 1–4C-alkyl or 1–4C-alkoxy,

R4 is a di-1–4C-alkylthiocarbamoyl radical, the radical —N(R7)R8 or an R9- and R10-substituted cyclic system or bicyclic system which is selected from the group consisting of benzene, furan, thiophene, thiazole, imidazole, tetrazole, pyridine and benzimidazole, R5 is hydrogen, R6 is hydrogen or 1–4C-alkyl, R7 and R8, together and including the nitrogen atom to which both are bonded, are an unsubstituted or substituted piperazino radical or a 1,2,3,4-tetrahydroisoquinoline radical, where a substituted piperazino radical is substituted by a substituent selected from the group consisting of —$C_pH_{(2p-2)}$—R14 and —$C_qH_{2q}$—R14, R9 is hydrogen, 1–4C-alkyl, halogen, nitro, carboxyl, 1–4C-alkoxycarbonyl or R15-substituted 1–4C-alkyl, R10 is hydrogen or 1–4C-alkyl, R14 is an R9- and R10-substituted cyclic system which is selected from the group consisting of benzene and thiophene, R15 is carboxyl, W is CH or N, X is S, Z is S, m is a number from 1 to 3, n is the number 0, t is the number 0, u is the number 0, 1 or 2, v is the number 0 or 1, p is the number 3 and q is the number 0 or 1 and their salts, where v is not the number 1 if m is the number 1, and where

R4 is not —N(R7)R8 or an N (nitrogen)-bonded cyclic system or bicyclic system if Z is S, v is the number 1 and u is the number 0.

One embodiment of the invention (embodiment a) are those compounds or those compounds of the formula I which are to be emphasized, particularly to be emphasized and which are exemplary, in which t is the number 0 and v is the number 0, and their salts.

A further embodiment of the invention (embodiment b) are those compounds or those compounds of the formula I which are to be emphasized, particularly to be emphasized and which are exemplary, in which t is the number 0, v is the number 1 and u is the number 0, and their salts.

A further embodiment of the invention (embodiment c) are those compounds or those compounds of the formula I which are to be emphasized, to be particularly emphasized and which are exemplary, in which t is the number 0, v is the number 1 and u is the number 1 or 2, and their salts.

Exemplary compounds according to the invention are listed in the following tables:

TABLE 1

Compounds of the formula I (see attached formula sheet) with W = CH, R = H, R1 = H, R2 = H, t = O, n = O, bonding of the pyridine ring in the 2-position, R4 = phenyl and the following further substituents and symbol meanings:

| R3 | R5 | R6 | X | m | Z | u | v |
|---|---|---|---|---|---|---|---|
| $CH_3$ | H | H | S | 1 | — | — | 0 |
| $CH_3$ | H | H | S | 2 | — | — | 0 |
| $CH_3$ | H | H | S | 3 | — | — | 0 |
| $CH_3$ | $CH_3$ | H | S | 3 | — | — | 0 |
| $OCH_3$ | H | H | S | 3 | — | — | 0 |
| $CH_3$ | H | $CH_3$ | S | 3 | — | — | 0 |
| $CH_3$ | H | H | O | 2 | — | — | 0 |
| $CH_3$ | H | H | O | 3 | — | — | 0 |
| $CH_3$ | H | H | N—$CH_3$ | 2 | — | — | 0 |
| $CH_3$ | H | H | N—$CH_3$ | 3 | — | — | 0 |
| $CH_3$ | H | H | S | 2 | S | 0 | 1 |
| $CH_3$ | H | H | S | 3 | S | 0 | 1 |
| $CH_3$ | $CH_3$ | H | S | 3 | S | 0 | 1 |
| $OCH_3$ | H | H | S | 3 | S | 0 | 1 |
| $CH_3$ | H | $CH_3$ | S | 3 | S | 0 | 1 |
| $CH_3$ | H | H | O | 2 | S | 0 | 1 |
| $CH_3$ | H | H | O | 3 | S | 0 | 1 |
| $CH_3$ | H | H | N—$CH_3$ | 2 | S | 0 | 1 |
| $CH_3$ | H | H | N—$CH_3$ | 3 | S | 0 | 1 |
| $CH_3$ | H | H | S | 2 | S | 1 | 1 |
| $CH_3$ | H | H | S | 3 | S | 1 | 1 |
| $CH_3$ | $CH_3$ | H | S | 3 | S | 1 | 1 |
| $OCH_3$ | H | H | S | 3 | S | 1 | 1 |
| $CH_3$ | H | $CH_3$ | S | 3 | S | 1 | 1 |
| $CH_3$ | H | H | O | 2 | S | 1 | 1 |
| $CH_3$ | H | H | O | 3 | S | 1 | 1 |
| $CH_3$ | H | H | N—$CH_3$ | 2 | S | 1 | 1 |
| $CH_3$ | H | H | N—$CH_3$ | 3 | S | 1 | 1 |

TABLE 2

Compounds of the formula I (see attached formula sheet) with W = CH, R = H, R1 = H, R2 = H, t = O, n = O, bonding of the pyridine ring in the 2-position, R4 = 2-furyl and the following further substituents and symbol meanings:

| R3 | R5 | R6 | X | m | Z | u | v |
|---|---|---|---|---|---|---|---|
| $CH_3$ | H | H | S | 1 | — | — | 0 |
| $CH_3$ | H | H | S | 2 | — | — | 0 |
| $CH_3$ | H | H | S | 3 | — | — | 0 |
| $CH_3$ | $CH_3$ | H | S | 3 | — | — | 0 |
| $OCH_3$ | H | H | S | 3 | — | — | 0 |
| $CH_3$ | H | $CH_3$ | S | 3 | — | — | 0 |
| $CH_3$ | H | H | O | 2 | — | — | 0 |
| $CH_3$ | H | H | O | 3 | — | — | 0 |
| $CH_3$ | H | H | N—$CH_3$ | 2 | — | — | 0 |
| $CH_3$ | H | H | N—$CH_3$ | 3 | — | — | 0 |
| $CH_3$ | H | H | S | 2 | S | 0 | 1 |
| $CH_3$ | H | H | S | 3 | S | 0 | 1 |
| $CH_3$ | $CH_3$ | H | S | 3 | S | 0 | 1 |
| $OCH_3$ | H | H | S | 3 | S | 0 | 1 |
| $CH_3$ | H | $CH_3$ | S | 3 | S | 0 | 1 |
| $CH_3$ | H | H | O | 2 | S | 0 | 1 |
| $CH_3$ | H | H | O | 3 | S | 0 | 1 |
| $CH_3$ | H | H | N—$CH_3$ | 2 | S | 0 | 1 |
| $CH_3$ | H | H | N—$CH_3$ | 3 | S | 0 | 1 |
| $CH_3$ | H | H | S | 2 | S | 1 | 1 |
| $CH_3$ | H | H | S | 3 | S | 1 | 1 |

TABLE 2-continued

Compounds of the formula I (see attached formula sheet) with W = CH, R = H, R1 = H, R2 = H, t = O, n = O, bonding of the pyridine ring in the 2-position, R4 = 2-furyl and the following further substituents and symbol meanings:

| R3 | R5 | R6 | X | m | Z | u | v |
|---|---|---|---|---|---|---|---|
| CH₃ | CH₃ | H | S | 3 | S | 1 | 1 |
| OCH₃ | H | H | S | 3 | S | 1 | 1 |
| CH₃ | H | CH₃ | S | 3 | S | 1 | 1 |
| CH₃ | H | H | O | 2 | S | 1 | 1 |
| CH₃ | H | H | O | 3 | S | 1 | 1 |
| CH₃ | H | H | N—CH₃ | 2 | S | 1 | 1 |
| CH₃ | H | H | N—CH₃ | 3 | S | 1 | 1 |

TABLE 3

Compounds of the formula I (see attached formula sheet) with W = CH, R = H, R1 = H, R2 = H, t = O, n = O, bonding of the pyridine ring in the 2-position, R4 = 4-methyl-5-thiazolyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |
| CH₃ | H | H | N—CH₃ | 3 | — | — | 0 |
| CH₃ | H | H | S | 2 | S | 0 | 1 |
| CH₃ | H | H | S | 3 | S | 0 | 1 |
| CH₃ | CH₃ | H | S | 3 | S | 0 | 1 |
| OCH₃ | H | H | S | 3 | S | 0 | 1 |
| CH₃ | H | CH₃ | S | 3 | S | 0 | 1 |
| CH₃ | H | H | O | 2 | S | 0 | 1 |
| CH₃ | H | H | O | 3 | S | 0 | 1 |
| CH₃ | H | H | N—CH₃ | 2 | S | 0 | 1 |
| CH₃ | H | H | N—CH₃ | 3 | S | 0 | 1 |
| CH₃ | H | H | S | 2 | S | 1 | 1 |
| CH₃ | H | H | S | 3 | S | 1 | 1 |
| CH₃ | CH₃ | H | S | 3 | S | 1 | 1 |
| OCH₃ | H | H | S | 3 | S | 1 | 1 |
| CH₃ | H | CH₃ | S | 3 | S | 1 | 1 |
| CH₃ | H | H | O | 2 | S | 1 | 1 |
| CH₃ | H | H | O | 3 | S | 1 | 1 |
| CH₃ | H | H | N—CH₃ | 2 | S | 1 | 1 |
| CH₃ | H | H | N—CH₃ | 3 | S | 1 | 1 |

TABLE 4

Compounds of the formula I (see attached formula sheet) with W = CH, R = H, R1 = H, R2 = H, t = O, n = O, bonding of the pyridine ring in the 2-position, R4 = 1-methyl-5-tetrazolyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |

TABLE 4-continued

Compounds of the formula I (see attached formula sheet) with W = CH, R = H, R1 = H, R2 = H, t = O, n = O, bonding of the pyridine ring in the 2-position, R4 = 1-methyl-5-tetrazolyl and the following further substituents and symbol meanings:

| R3 | R5 | R6 | X | m | Z | u | v |
|---|---|---|---|---|---|---|---|
| CH₃ | H | H | N—CH₃ | 3 | — | — | 0 |
| CH₃ | H | H | S | 2 | S | 0 | 1 |
| CH₃ | H | H | S | 3 | S | 0 | 1 |
| CH₃ | CH₃ | H | S | 3 | S | 0 | 1 |
| OCH₃ | H | H | S | 3 | S | 0 | 1 |
| CH₃ | H | CH | S | 3 | S | 0 | 1 |
| CH₃ | H | H | O | 2 | S | 0 | 1 |
| CH₃ | H | H | O | 3 | S | 0 | 1 |
| CH₃ | H | H | N—CH₃ | 2 | S | 0 | 1 |
| CH₃ | H | H | N—CH₃ | 3 | S | 0 | 1 |
| CH₃ | H | H | S | 2 | S | 1 | 1 |
| CH₃ | H | H | S | 3 | S | 1 | 1 |
| CH₃ | CH₃ | H | S | 3 | S | 1 | 1 |
| OCH₃ | H | H | S | 3 | S | 1 | 1 |
| CH₃ | H | CH₃ | S | 3 | S | 1 | 1 |
| CH₃ | H | H | O | 2 | S | 1 | 1 |
| CH₃ | H | H | O | 3 | S | 1 | 1 |
| CH₃ | H | H | N—CH₃ | 2 | S | 1 | 1 |
| CH₃ | H | H | N—CH₃ | 3 | S | 1 | 1 |

TABLE 5

Compounds of the formula I (see attached formula sheet) with W = CH, R = H, R1 = H, R2 = H, t = O, n = O, bonding of the pyridine ring in the 2-position, R4 = 4-pyridinyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |
| CH₃ | H | H | N—CH₃ | 3 | — | — | 0 |
| CH₃ | H | H | S | 2 | S | 0 | 1 |
| CH₃ | H | H | S | 3 | S | 0 | 1 |
| CH₃ | CH₃ | H | S | 3 | S | 0 | 1 |
| OCH₃ | H | H | S | 3 | S | 0 | 1 |
| CH₃ | H | CH₃ | S | 3 | S | 0 | 1 |
| CH₃ | H | H | O | 2 | S | 0 | 1 |
| CH₃ | H | H | O | 3 | S | 0 | 1 |
| CH₃ | H | H | N—CH₃ | 2 | S | 0 | 1 |
| CH₃ | H | H | N—CH₃ | 3 | S | 0 | 1 |
| CH₃ | H | H | S | 2 | S | 1 | 1 |
| CH₃ | H | H | S | 3 | S | 1 | 1 |
| CH₃ | CH₃ | H | S | 3 | S | 1 | 1 |
| OCH₃ | H | H | S | 3 | S | 1 | 1 |
| CH₃ | H | CH₃ | S | 3 | S | 1 | 1 |
| CH₃ | H | H | O | 2 | S | 1 | 1 |
| CH₃ | H | H | O | 3 | S | 1 | 1 |
| CH₃ | H | H | N—CH₃ | 2 | S | 1 | 1 |
| CH₃ | H | H | N—CH₃ | 3 | S | 1 | 1 |

TABLE 6

Compounds of the formula I (see attached formula sheet) with W = CH, R = H, R1 = H, R2 = H, t = O, n = O, bonding of the pyridine ring in the 2-position, R4 = 4-benzyl-1-piperazinyl and the following further substituents and symbol meanings:

| R3 | R5 | R6 | X | m | Z | u | v |
|---|---|---|---|---|---|---|---|
| CH$_3$ | H | H | S | 1 | — | — | 0 |
| CH$_3$ | H | H | S | 2 | — | — | 0 |
| CH$_3$ | H | H | S | 3 | — | — | 0 |
| CH$_3$ | CH$_3$ | H | S | 3 | — | — | 0 |
| OCH$_3$ | H | H | S | 3 | — | — | 0 |
| CH$_3$ | H | CH$_3$ | S | 3 | — | — | 0 |
| CH$_3$ | H | H | O | 2 | — | — | 0 |
| CH$_3$ | H | H | O | 3 | — | — | 0 |
| CH$_3$ | H | H | N—CH$_3$ | 2 | — | — | 0 |
| CH$_3$ | H | H | N—CH$_3$ | 3 | — | — | 0 |
| CH$_3$ | H | H | S | 2 | S | 2 | 1 |
| CH$_3$ | H | H | S | 3 | S | 2 | 1 |
| CH$_3$ | CH$_3$ | H | S | 3 | S | 2 | 1 |
| OCH$_3$ | H | H | S | 3 | S | 2 | 1 |
| CH$_3$ | H | CH$_3$ | S | 3 | S | 2 | 1 |
| CH$_3$ | H | H | O | 2 | S | 2 | 1 |
| CH$_3$ | H | H | O | 3 | S | 2 | 1 |
| CH$_3$ | H | H | N—CH$_3$ | 2 | S | 2 | 1 |
| CH$_3$ | H | H | N—CH$_3$ | 3 | S | 2 | 1 |
| CH$_3$ | H | H | S | 2 | S | 3 | 1 |
| CH$_3$ | H | H | S | 3 | S | 3 | 1 |
| CH$_3$ | CH$_3$ | H | S | 3 | S | 3 | 1 |
| OCH$_3$ | H | H | S | 3 | S | 3 | 1 |
| CH$_3$ | H | CH$_3$ | S | 3 | S | 3 | 1 |
| CH$_3$ | H | H | O | 2 | S | 3 | 1 |
| CH$_3$ | H | H | O | 3 | S | 3 | 1 |
| CH$_3$ | H | H | N—CH$_3$ | 2 | S | 3 | 1 |
| CH$_3$ | H | H | N—CH$_3$ | 3 | S | 3 | 1 |

TABLE 7

Compounds of the formula I (see attached formula sheet) with W = CH, R = H, R1 = H, R2 = H, t = O, n = O, bonding of the pyridine ring in the 2-position, R4 = 4-phenyl-1-piperazinyl and the following further substituents and symbol meanings:

| R3 | R5 | R6 | X | m | Z | u | v |
|---|---|---|---|---|---|---|---|
| CH$_3$ | H | H | S | 1 | — | — | 0 |
| CH$_3$ | H | H | S | 2 | — | — | 0 |
| CH$_3$ | H | H | S | 3 | — | — | 0 |
| CH$_3$ | CH$_3$ | H | S | 3 | — | — | 0 |
| OCH$_3$ | H | H | S | 3 | — | — | 0 |
| CH$_3$ | H | CH$_3$ | S | 3 | — | — | 0 |
| CH$_3$ | H | H | O | 2 | — | — | 0 |
| CH$_3$ | H | H | O | 3 | — | — | 0 |
| CH$_3$ | H | H | N—CH$_3$ | 2 | — | — | 0 |
| CH$_3$ | H | H | N—CH$_3$ | 3 | — | — | 0 |
| CH$_3$ | H | H | S | 2 | S | 2 | 1 |
| CH$_3$ | H | H | S | 3 | S | 2 | 1 |
| CH$_3$ | CH$_3$ | H | S | 3 | S | 2 | 1 |
| OCH$_3$ | H | H | S | 3 | S | 2 | 1 |
| CH$_3$ | H | CH$_3$ | S | 3 | S | 2 | 1 |
| CH$_3$ | H | H | O | 2 | S | 2 | 1 |
| CH$_3$ | H | H | O | 3 | S | 2 | 1 |
| CH$_3$ | H | H | N—CH$_3$ | 2 | S | 2 | 1 |
| CH$_3$ | H | H | N—CH$_3$ | 3 | S | 2 | 1 |
| CH$_3$ | H | H | S | 2 | S | 3 | 1 |
| CH$_3$ | H | H | S | 3 | S | 3 | 1 |
| CH$_3$ | CH$_3$ | H | S | 3 | S | 3 | 1 |
| OCH$_3$ | H | H | S | 3 | S | 3 | 1 |
| CH$_3$ | H | CH$_3$ | S | 3 | S | 3 | 1 |
| CH$_3$ | H | H | O | 2 | S | 3 | 1 |
| CH$_3$ | H | H | O | 3 | S | 3 | 1 |
| CH$_3$ | H | H | N—CH$_3$ | 2 | S | 3 | 1 |
| CH$_3$ | H | H | N—CH$_3$ | 3 | S | 3 | 1 |

TABLE 8

Compounds of the formula I (see attached formula sheet) with W = CH, R = H, R1 = H, R2 = H, t = O, n = O, bonding of the pyridine ring in the 2-position, R4 = 1,2,3,4-tetrahydroisoquinolin-2-yl and the following further substituents and symbol meanings:

| R3 | R5 | R6 | X | m | Z | u | v |
|---|---|---|---|---|---|---|---|
| CH$_3$ | H | H | S | 1 | — | — | 0 |
| CH$_3$ | H | H | S | 2 | — | — | 0 |
| CH$_3$ | H | H | S | 3 | — | — | 0 |
| CH$_3$ | CH$_3$ | H | S | 3 | — | — | 0 |
| OCH$_3$ | H | H | S | 3 | — | — | 0 |
| CH$_3$ | H | CH$_3$ | S | 3 | — | — | 0 |
| CH$_3$ | H | H | O | 2 | — | — | 0 |
| CH$_3$ | H | H | O | 3 | — | — | 0 |
| CH$_3$ | H | H | N—CH$_3$ | 2 | — | — | 0 |
| CH$_3$ | H | H | N—CH$_3$ | 3 | — | — | 0 |
| CH$_3$ | H | H | S | 2 | S | 2 | 1 |
| CH$_3$ | H | H | S | 3 | S | 2 | 1 |
| CH$_3$ | CH$_3$ | H | S | 3 | S | 2 | 1 |
| OCH$_3$ | H | H | S | 3 | S | 2 | 1 |
| CH$_3$ | H | CH$_3$ | S | 3 | S | 2 | 1 |
| CH$_3$ | H | H | O | 2 | S | 2 | 1 |
| CH$_3$ | H | H | O | 3 | S | 2 | 1 |
| CH$_3$ | H | H | N—CH$_3$ | 2 | S | 2 | 1 |
| CH$_3$ | H | H | N—CH$_3$ | 3 | S | 2 | 1 |
| CH$_3$ | H | H | S | 2 | S | 3 | 1 |
| CH$_3$ | H | H | S | 3 | S | 3 | 1 |
| CH$_3$ | CH$_3$ | H | S | 3 | S | 3 | 1 |
| OCH$_3$ | H | H | S | 3 | S | 3 | 1 |
| CH$_3$ | H | CH$_3$ | S | 3 | S | 3 | 1 |
| CH$_3$ | H | H | O | 2 | S | 3 | 1 |
| CH$_3$ | H | H | O | 3 | S | 3 | 1 |
| CH$_3$ | H | H | N—CH$_3$ | 2 | S | 3 | 1 |
| CH$_3$ | H | H | N—CH$_3$ | 3 | S | 3 | 1 |

TABLE 9

Compounds of the formula I (see attached formula sheet) with W = CH, R = H, R1 = H, R2 = H, t = O, n = O, bonding of the pyridine ring in the 2-position, R4 = dimethylthiocarbamoyl and the following further substituents and symbol meanings:

| R3 | R5 | R6 | X | m | Z | u | v |
|---|---|---|---|---|---|---|---|
| CH$_3$ | H | H | S | 1 | — | — | 0 |
| CH$_3$ | H | H | S | 2 | — | — | 0 |
| CH$_3$ | H | H | S | 3 | — | — | 0 |
| CH$_3$ | CH$_3$ | H | S | 3 | — | — | 0 |
| OCH$_3$ | H | H | S | 3 | — | — | 0 |
| CH$_3$ | H | CH$_3$ | S | 3 | — | — | 0 |
| CH$_3$ | H | H | O | 2 | — | — | 0 |
| CH$_3$ | H | H | O | 3 | — | — | 0 |
| CH$_3$ | H | H | N—CH$_3$ | 2 | — | — | 0 |
| CH$_3$ | H | H | N—CH$_3$ | 3 | — | — | 0 |
| CH$_3$ | H | H | S | 2 | S | 0 | 1 |
| CH$_3$ | H | H | S | 3 | S | 0 | 1 |
| CH$_3$ | CH$_3$ | H | S | 3 | S | 0 | 1 |
| OCH$_3$ | H | H | S | 3 | S | 0 | 1 |
| CH$_3$ | H | CH$_3$ | S | 3 | S | 0 | 1 |
| CH$_3$ | H | H | O | 2 | S | 0 | 1 |
| CH$_3$ | H | H | O | 3 | S | 0 | 1 |
| CH$_3$ | H | H | N—CH$_3$ | 2 | S | 0 | 1 |
| CH$_3$ | H | H | N—CH$_3$ | 3 | S | 0 | 1 |
| CH$_3$ | H | H | S | 2 | N—CH$_3$ | 0 | 1 |
| CH$_3$ | H | H | S | 3 | N—CH$_3$ | 0 | 1 |
| CH$_3$ | CH$_3$ | H | S | 3 | N—CH$_3$ | 0 | 1 |
| OCH$_3$ | H | H | S | 3 | N—CH$_3$ | 0 | 1 |
| CH$_3$ | H | CH$_3$ | S | 3 | N—CH$_3$ | 0 | 1 |
| CH$_3$ | H | H | O | 2 | N—CH$_3$ | 0 | 1 |
| CH$_3$ | H | H | O | 3 | N—CH$_3$ | 0 | 1 |
| CH$_3$ | H | H | N—CH$_3$ | 2 | N—CH$_3$ | 0 | 1 |
| CH$_3$ | H | H | N—CH$_3$ | 3 | N—CH$_3$ | 0 | 1 |

TABLE 10

Compounds of the formula I (see attached formula sheet) with W = CH, R = H, R1 = H, R2 = H, t = O, n = O, bonding of the pyridine ring in the 2-position, R4 = 1-imidazolyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH | H | H | N—CH₃ | 2 | — | — | 0 |
| CH₃ | H | H | N—CH₃ | 3 | — | — | 0 |
| CH₃ | H | H | S | 2 | S | 2 | 1 |
| CH₃ | H | H | S | 3 | S | 2 | 1 |
| CH₃ | CH₃ | H | S | 3 | S | 2 | 1 |
| OCH₃ | H | H | S | 3 | S | 2 | 1 |
| CH₃ | H | CH₃ | S | 3 | S | 2 | 1 |
| CH₃ | H | H | O | 2 | S | 2 | 1 |
| CH₃ | H | H | O | 3 | S | 2 | 1 |
| CH₃ | H | H | N—CH₃ | 2 | S | 2 | 1 |
| CH₃ | H | H | N—CH₃ | 3 | S | 2 | 1 |
| CH₃ | H | H | S | 2 | S | 3 | 1 |
| CH₃ | H | H | S | 3 | S | 3 | 1 |
| CH₃ | CH₃ | H | S | 3 | S | 3 | 1 |
| OCH₃ | H | H | S | 3 | S | 3 | 1 |
| CH₃ | H | CH₃ | S | 3 | S | 3 | 1 |
| CH₃ | H | H | O | 2 | S | 3 | 1 |
| CH₃ | H | H | O | 3 | S | 3 | 1 |
| CH₃ | H | H | N—CH₃ | 2 | S | 3 | 1 |
| CH₃ | H | H | N—CH₃ | 3 | S | 3 | 1 |

TABLE 11

Compounds of the formula I (see attached formula sheet) with W = CH, R = H, R1 = H, R2 = H, t = O, n = O, bonding of the pyridine ring in the 2-position, R4 = 4-(5-chloro-2-thienylmethyl)-1-piperazinyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |
| CH₃ | H | H | N—CH₃ | 3 | — | — | 0 |
| CH₃ | H | H | S | 2 | S | 2 | 1 |
| CH₃ | H | H | S | 3 | S | 2 | 1 |
| CH₃ | CH₃ | H | S | 3 | S | 2 | 1 |
| OCH₃ | H | H | S | 3 | S | 2 | 1 |
| CH₃ | H | CH₃ | S | 3 | S | 2 | 1 |
| CH₃ | H | H | O | 2 | S | 2 | 1 |
| CH₃ | H | H | O | 3 | S | 2 | 1 |
| CH₃ | H | H | N—CH₃ | 2 | S | 2 | 1 |
| CH₃ | H | H | N—CH₃ | 3 | S | 2 | 1 |
| CH₃ | H | H | S | 2 | S | 3 | 1 |
| CH₃ | H | H | S | 3 | S | 3 | 1 |
| CH₃ | CH₃ | H | S | 3 | S | 3 | 1 |
| OCH₃ | H | H | S | 3 | S | 3 | 1 |
| CH₃ | H | CH₃ | S | 3 | S | 3 | 1 |
| CH₃ | H | H | O | 2 | S | 3 | 1 |
| CH₃ | H | H | O | 3 | S | 3 | 1 |
| CH₃ | H | H | N—CH₃ | 2 | S | 3 | 1 |
| CH₃ | H | H | N—CH₃ | 3 | S | 3 | 1 |

TABLE 12

Compounds of the formula I (see attached formula sheet) with W = CH, R = H, R1 = H, R2 = H, t = O, n = O, bonding of the pyridine ring in the 2-position, R4 = 2-benzimidazolyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |
| CH₃ | H | H | N—CH₃ | 3 | — | — | 0 |
| CH₃ | H | H | S | 2 | S | 0 | 1 |
| CH₃ | H | H | S | 3 | S | 0 | 1 |
| CH₃ | CH₃ | H | S | 3 | S | 0 | 1 |
| OCH₃ | H | H | S | 3 | S | 0 | 1 |
| CH₃ | H | CH₃ | S | 3 | S | 0 | 1 |
| CH₃ | H | H | O | 2 | S | 0 | 1 |
| CH₃ | H | H | O | 3 | S | 0 | 1 |
| CH₃ | H | H | N—CH₃ | 2 | S | 0 | 1 |
| CH₃ | H | H | N—CH₃ | 3 | S | 0 | 1 |
| CH₃ | H | H | S | 2 | S | 1 | 1 |
| CH₃ | H | H | S | 3 | S | 1 | 1 |
| CH₃ | CH₃ | H | S | 3 | S | 1 | 1 |
| OCH₃ | H | H | S | 3 | S | 1 | 1 |
| CH₃ | H | CH₃ | S | 3 | S | 1 | 1 |
| CH₃ | H | H | O | 2 | S | 1 | 1 |
| CH₃ | H | H | O | 3 | S | 1 | 1 |
| CH₃ | H | H | N—CH₃ | 2 | S | 1 | 1 |
| CH₃ | H | H | N—CH₃ | 3 | S | 1 | 1 |

TABLE 13

Compounds of the formula I (see attached formula sheet) with W = CH, R = H, R1 = H, R2 = H, t = O, n = O, bonding of the pyridine ring in the 2-position, R4 = 2-methoxycarbonylphenyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |
| CH₃ | H | H | N—CH₃ | 3 | — | — | 0 |
| CH₃ | H | H | S | 2 | S | 0 | 1 |
| CH₃ | H | H | S | 3 | S | 0 | 1 |
| CH₃ | CH₃ | H | S | 3 | S | 0 | 1 |
| OCH₃ | H | H | S | 3 | S | 0 | 1 |
| CH₃ | H | CH₃ | S | 3 | S | 0 | 1 |
| CH₃ | H | H | O | 2 | S | 0 | 1 |
| CH₃ | H | H | O | 3 | S | 0 | 1 |
| CH₃ | H | H | N—CH₃ | 2 | S | 0 | 1 |
| CH₃ | H | H | N—CH₃ | 3 | S | 0 | 1 |
| CH₃ | H | H | S | 2 | S | 1 | 1 |
| CH₃ | H | H | S | 3 | S | 1 | 1 |
| CH₃ | CH₃ | H | S | 3 | S | 1 | 1 |
| OCH₃ | H | H | S | 3 | S | 1 | 1 |
| CH₃ | H | CH₃ | S | 3 | S | 1 | 1 |
| CH₃ | H | H | O | 2 | S | 1 | 1 |
| CH₃ | H | H | O | 3 | S | 1 | 1 |
| CH₃ | H | H | N—CH₃ | 2 | S | 1 | 1 |
| CH₃ | H | H | N—CH₃ | 3 | S | 1 | 1 |

TABLE 14

Compounds of the formula I (see attached formula sheet) with W = CH, R = H, R1 = H, R2 = H, t = O, n = O, bonding of the pyridine ring in the 2-position, R4 = 2-methyl-5-nitro-1-imidazolyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |
| CH₃ | H | H | N—CH₃ | 3 | — | — | 0 |
| CH₃ | H | H | S | 2 | S | 2 | 1 |
| CH₃ | H | H | S | 3 | S | 2 | 1 |
| CH₃ | CH₃ | H | S | 3 | S | 2 | 1 |
| OCH₃ | H | H | S | 3 | S | 2 | 1 |
| CH₃ | H | CH₃ | S | 3 | S | 2 | 1 |
| CH₃ | H | H | O | 2 | S | 2 | 1 |
| CH₃ | H | H | O | 3 | S | 2 | 1 |
| CH₃ | H | H | N—CH₃ | 2 | S | 2 | 1 |
| CH₃ | H | H | N—CH₃ | 3 | S | 2 | 1 |
| CH₃ | H | H | S | 2 | S | 3 | 1 |
| CH₃ | H | H | S | 3 | S | 3 | 1 |
| CH₃ | CH₃ | H | S | 3 | S | 3 | 1 |
| OCH₃ | H | H | S | 3 | S | 3 | 1 |
| CH₃ | H | CH₃ | S | 3 | S | 3 | 1 |
| CH₃ | H | H | O | 2 | S | 3 | 1 |
| CH₃ | H | H | O | 3 | S | 3 | 1 |
| CH₃ | H | H | N—CH₃ | 2 | S | 3 | 1 |
| CH₃ | H | H | N—CH₃ | 3 | S | 3 | 1 |

TABLE 15

Compounds of the formula I (see attached formula sheet) with W = CH, R = H, R1 = H, R2 = H, t = O, n = O, bonding of the pyridine ring in the 2-position, R4 = 5-chloro-2-thienyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |
| CH₃ | H | H | N—CH₃ | 3 | — | — | 0 |
| CH₃ | H | H | S | 2 | S | 0 | 1 |
| CH₃ | H | H | S | 3 | S | 0 | 1 |
| CH₃ | CH₃ | H | S | 3 | S | 0 | 1 |
| OCH₃ | H | H | S | 3 | S | 0 | 1 |
| CH₃ | H | CH₃ | S | 3 | S | 0 | 1 |
| CH₃ | H | H | O | 2 | S | 0 | 1 |
| CH₃ | H | H | O | 3 | S | 0 | 1 |
| CH₃ | H | H | N—CH₃ | 2 | S | 0 | 1 |
| CH₃ | H | H | N—CH₃ | 3 | S | 0 | 1 |
| CH₃ | H | H | S | 2 | S | 1 | 1 |
| CH₃ | H | H | S | 3 | S | 1 | 1 |
| CH₃ | CH₃ | H | S | 3 | S | 1 | 1 |
| OCH₃ | H | H | S | 3 | S | 1 | 1 |
| CH₃ | H | CH₃ | S | 3 | S | 1 | 1 |
| CH₃ | H | H | O | 2 | S | 1 | 1 |
| CH₃ | H | H | O | 3 | S | 1 | 1 |
| CH₃ | H | H | N—CH₃ | 2 | S | 1 | 1 |
| CH₃ | H | H | N—CH₃ | 3 | S | 1 | 1 |

TABLE 16

Compounds of the formula I (see attached formula sheet) with W = CH, R = H, R1 = H, R2 = H, t = 0, n = 0, bonding of the pyridine ring in the 2-position, R4 = 2-pyridine-3-carboxylic acid and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |
| CH₃ | H | H | N—CH₃ | 3 | — | — | 0 |
| CH₃ | H | H | S | 2 | S | 0 | 1 |
| CH₃ | H | H | S | 3 | S | 0 | 1 |
| CH₃ | CH₃ | H | S | 3 | S | 0 | 1 |
| OCH₃ | H | H | S | 3 | S | 0 | 1 |
| CH₃ | H | CH₃ | S | 3 | S | 0 | 1 |
| CH₃ | H | H | O | 2 | S | 0 | 1 |
| CH₃ | H | H | O | 3 | S | 0 | 1 |
| CH₃ | H | H | N—CH₃ | 2 | S | 0 | 1 |
| CH₃ | H | H | N—CH₃ | 3 | S | 0 | 1 |
| CH₃ | H | H | S | 2 | S | 1 | 1 |
| CH₃ | H | H | S | 3 | S | 1 | 1 |
| CH₃ | CH₃ | H | S | 3 | S | 1 | 1 |
| OCH₃ | H | H | S | 3 | S | 1 | 1 |
| CH₃ | H | CH₃ | S | 3 | S | 1 | 1 |
| CH₃ | H | H | O | 2 | S | 1 | 1 |
| CH₃ | H | H | O | 3 | S | 1 | 1 |
| CH₃ | H | H | N—CH₃ | 2 | S | 1 | 1 |
| CH₃ | H | H | N—CH₃ | 3 | S | 1 | 1 |

TABLE 17

Compounds of the formula I (see attached formula sheet) with W = CH, R = H, R1 = H, R2 = H, t = 0, n = 0, bonding of the pyridine ring in the 2-position, R4 = 2-thiazolyl and the following further substituents and symbol meanings:

| R3 | R5 | R6 | X | m | Z | u | v |
|---|---|---|---|---|---|---|---|
| CH₃ | H | H | S | 1 | — | — | 0 |
| CH₃ | H | H | S | 2 | — | — | 0 |
| CH₃ | H | H | S | 3 | — | — | 0 |
| CH₃ | CH₃ | H | S | 3 | — | — | 0 |
| OCH₃ | H | H | S | 3 | — | — | 0 |
| CH₃ | H | CH₃ | S | 3 | — | — | 0 |
| CH₃ | H | H | O | 2 | — | — | 0 |
| CH₃ | H | H | O | 3 | — | — | 0 |
| CH₃ | H | H | N—CH₃ | 2 | — | — | 0 |
| CH₃ | H | H | N—CH₃ | 3 | — | — | 0 |
| CH₃ | H | H | S | 2 | S | 0 | 1 |
| CH₃ | H | H | S | 3 | S | 0 | 1 |
| CH₃ | CH₃ | H | S | 3 | S | 0 | 1 |
| OCH₃ | H | H | S | 3 | S | 0 | 1 |
| CH₃ | H | CH₃ | S | 3 | S | 0 | 1 |
| CH₃ | H | H | O | 2 | S | 0 | 1 |
| CH₃ | H | H | O | 3 | S | 0 | 1 |
| CH₃ | H | H | N—CH₃ | 2 | S | 0 | 1 |
| CH₃ | H | H | N—CH₃ | 3 | S | 0 | 1 |
| CH₃ | H | H | S | 2 | S | 1 | 1 |
| CH₃ | H | H | S | 3 | S | 1 | 1 |
| CH₃ | CH₃ | H | S | 3 | S | 1 | 1 |
| OCH₃ | H | H | S | 3 | S | 1 | 1 |
| CH₃ | H | CH₃ | S | 3 | S | 1 | 1 |
| CH₃ | H | H | O | 2 | S | 1 | 1 |
| CH₃ | H | H | O | 3 | S | 1 | 1 |
| CH₃ | H | H | N—CH₃ | 2 | S | 1 | 1 |
| CH₃ | H | H | N—CH₃ | 3 | S | 1 | 1 |

TABLE 18

Compounds of the formula I (see attached formula sheet) with W = CH, R = H, R1 = H, R2 = H, t = 0, n = 0, bonding of the pyridine ring in the 2-position, R4 = 2-imidazolyl and the following further substituents and symbol meanings:

| R3 | R5 | R6 | X | m | Z | u | v |
|---|---|---|---|---|---|---|---|
| CH$_3$ | H | H | S | 1 | — | — | 0 |
| CH$_3$ | H | H | S | 2 | — | — | 0 |
| CH$_3$ | H | H | S | 3 | — | — | 0 |
| CH$_3$ | CH$_3$ | H | S | 3 | — | — | 0 |
| OCH$_3$ | H | H | S | 3 | — | — | 0 |
| CH$_3$ | H | CH$_3$ | S | 3 | — | — | 0 |
| CH$_3$ | H | H | O | 2 | — | — | 0 |
| CH$_3$ | H | H | O | 3 | — | — | 0 |
| CH$_3$ | H | H | N—CH$_3$ | 2 | — | — | 0 |
| CH$_3$ | H | H | N—CH$_3$ | 3 | — | — | 0 |
| CH$_3$ | H | H | S | 2 | S | 0 | 1 |
| CH$_3$ | H | H | S | 3 | S | 0 | 1 |
| CH$_3$ | CH$_3$ | H | S | 3 | S | 0 | 1 |
| OCH$_3$ | H | H | S | 3 | S | 0 | 1 |
| CH$_3$ | H | CH$_3$ | S | 3 | S | 0 | 1 |
| CH$_3$ | H | H | O | 2 | S | 0 | 1 |
| CH$_3$ | H | H | O | 3 | S | 0 | 1 |
| CH$_3$ | H | H | N—CH$_3$ | 2 | S | 0 | 1 |
| CH$_3$ | H | H | N—CH$_3$ | 3 | S | 0 | 1 |
| CH$_3$ | H | H | S | 2 | S | 1 | 1 |
| CH$_3$ | H | H | S | 3 | S | 1 | 1 |
| CH$_3$ | CH$_3$ | H | S | 3 | S | 1 | 1 |
| OCH$_3$ | H | H | S | 3 | S | 1 | 1 |
| CH$_3$ | H | CH$_3$ | S | 3 | S | 1 | 1 |
| CH$_3$ | H | H | O | 2 | S | 1 | 1 |
| CH$_3$ | H | H | O | 3 | S | 1 | 1 |
| CH$_3$ | H | H | N—CH$_3$ | 2 | S | 1 | 1 |
| CH$_3$ | H | H | N—CH$_3$ | 3 | S | 1 | 1 |

TABLE 19

Compounds of the formula I (see attached formula sheet) with W = CH, R = H, R1 = H, R2 = H, t = 0, n = 0, bonding of the pyridine ring in the 2-position, R4 = 5-nitro-1-imidazolyl and the following further substituents and symbol meanings:

| R3 | R5 | R6 | X | m | Z | u | v |
|---|---|---|---|---|---|---|---|
| CH$_3$ | H | H | S | 1 | — | — | 0 |
| CH$_3$ | H | H | S | 2 | — | — | 0 |
| CH$_3$ | H | H | S | 3 | — | — | 0 |
| CH$_3$ | CH$_3$ | H | S | 3 | — | — | 0 |
| OCH$_3$ | H | H | S | 3 | — | — | 0 |
| CH$_3$ | H | CH$_3$ | S | 3 | — | — | 0 |
| CH$_3$ | H | H | O | 2 | — | — | 0 |
| CH$_3$ | H | H | O | 3 | — | — | 0 |
| CH$_3$ | H | H | N—CH$_3$ | 2 | — | — | 0 |
| CH$_3$ | H | H | N—CH$_3$ | 3 | — | — | 0 |
| CH$_3$ | H | H | S | 2 | S | 2 | 1 |
| CH$_3$ | H | H | S | 3 | S | 2 | 1 |
| CH$_3$ | CH$_3$ | H | S | 3 | S | 2 | 1 |
| OCH$_3$ | H | H | S | 3 | S | 2 | 1 |
| CH$_3$ | H | CH$_3$ | S | 3 | S | 2 | 1 |
| CH$_3$ | H | H | O | 2 | S | 2 | 1 |
| CH$_3$ | H | H | O | 3 | S | 2 | 1 |
| CH$_3$ | H | H | N—CH$_3$ | 2 | S | 2 | 1 |
| CH$_3$ | H | H | N—CH$_3$ | 3 | S | 2 | 1 |
| CH$_3$ | H | H | S | 2 | S | 3 | 1 |
| CH$_3$ | H | H | S | 3 | S | 3 | 1 |
| CH$_3$ | CH$_3$ | H | S | 3 | S | 3 | 1 |
| OCH$_3$ | H | H | S | 3 | S | 3 | 1 |
| CH$_3$ | H | CH$_3$ | S | 3 | S | 3 | 1 |
| CH$_3$ | H | H | O | 2 | S | 3 | 1 |
| CH$_3$ | H | H | O | 3 | S | 3 | 1 |
| CH$_3$ | H | H | N—CH$_3$ | 2 | S | 3 | 1 |
| CH$_3$ | H | H | N—CH$_3$ | 3 | S | 3 | 1 |

TABLE 20

Compounds of the formula I (see attached formula sheet) with W = CH, R = H, R1 = H, R2 = H, t = 0, n = 0, bonding of the pyridine ring in the 2-position, R4 = 2-pyridinyl and the following further substituents and symbol meanings:

| R3 | R5 | R6 | X | m | Z | u | v |
|---|---|---|---|---|---|---|---|
| CH$_3$ | H | H | S | 1 | — | — | 0 |
| CH$_3$ | H | H | S | 2 | — | — | 0 |
| CH$_3$ | H | H | S | 3 | — | — | 0 |
| CH$_3$ | CH$_3$ | H | S | 3 | — | — | 0 |
| OCH$_3$ | H | H | S | 3 | — | — | 0 |
| CH$_3$ | H | CH$_3$ | S | 3 | — | — | 0 |
| CH$_3$ | H | H | O | 2 | — | — | 0 |
| CH$_3$ | H | H | O | 3 | — | — | 0 |
| CH$_3$ | H | H | N—CH$_3$ | 2 | — | — | 0 |
| CH$_3$ | H | H | N—CH$_3$ | 3 | — | — | 0 |
| CH$_3$ | H | H | S | 2 | S | 0 | 1 |
| CH$_3$ | H | H | S | 3 | S | 0 | 1 |
| CH$_3$ | CH$_3$ | H | S | 3 | S | 0 | 1 |
| OCH$_3$ | H | H | S | 3 | S | 0 | 1 |
| CH$_3$ | H | CH$_3$ | S | 3 | S | 0 | 1 |
| CH$_3$ | H | H | O | 2 | S | 0 | 1 |
| CH$_3$ | H | H | O | 3 | S | 0 | 1 |
| CH$_3$ | H | H | N—CH$_3$ | 2 | S | 0 | 1 |
| CH$_3$ | H | H | N—CH$_3$ | 3 | S | 0 | 1 |
| CH$_3$ | H | H | S | 2 | S | 1 | 1 |
| CH$_3$ | H | H | S | 3 | S | 1 | 1 |
| CH$_3$ | CH$_3$ | H | S | 3 | S | 1 | 1 |
| OCH$_3$ | H | H | S | 3 | S | 1 | 1 |
| CH$_3$ | H | CH$_3$ | S | 3 | S | 1 | 1 |
| CH$_3$ | H | H | O | 2 | S | 1 | 1 |
| CH$_3$ | H | H | O | 3 | S | 1 | 1 |
| CH$_3$ | H | H | N—CH$_3$ | 2 | S | 1 | 1 |
| CH$_3$ | H | H | N—CH$_3$ | 3 | S | 1 | 1 |

TABLE 21–TABLE 40

Compounds of the formula I (see attached formula sheet) as defined in Tables 1–20, but with bonding of the pyridine ring in the 4-position, and the salts of the compounds in Tables 1–40.

The invention further relates to a process for the preparation of the compounds of the formula I and their salts.

The process comprises a) reacting mercapto compounds of the formula II (see attached formula sheet), in which R and W have the meanings indicated above, with pyridine derivatives III (see attached formula sheet), in which R1, R2, R3, R4, R5, R6, X, Y, Z, m, r, t, u and v have the meanings indicated above and A is a suitable leaving group, or b) reacting compounds of the formula IV (see attached formula sheet), in which W, R, R1, R2, R3, R5, R6, X, m and n have the meanings indicated above and A is a suitable leaving group, with compounds of the formula V (see attached formula sheet), in which R4, Y, Z, r, t, u and v have the meanings indicated above, and (if compounds of the formula I where n=1 or 2 and/or Y=SO or SO$_2$ and/or Z=SO or SO$_2$ are the desired final products) then oxidizing the compounds obtained where n=0 and/or Y=S and/or Z=S, and/or if desired then converting compounds obtained into the salts and/or if desired then converting salts obtained into the free compounds.

In the abovementioned reactions, the starting compounds can be employed as such or optionally in the form of their salts.

Suitable leaving groups A which may be mentioned are, for example, halogen atoms, in particular chlorine, or hydroxyl groups activated by esterification (e.g. with p-toluenesulfonic acid).

The reaction of II with III is carried out in suitable, preferably polar, protic or aprotic solvents (such as methanol, ethanol, isopropanol, dimethyl sulfoxide, acetone, dimethylformamide or acetonitrile) in the presence of or with exclusion of water. It is carried out, for example, in the presence of a proton acceptor, if desired with addition of catalytic amounts of an iodide, such as sodium iodide. Suitable proton acceptors are alkali metal hydroxides, such as sodium hydroxide, alkali metal carbonates, such as potassium carbonate, or tertiary amines, such as pyridine, triethylamine or ethyldiisopropylamine. Alternatively, the reaction can also be carried out without a proton acceptor, where—depending on the nature of the starting compounds—the acid addition salts can optionally first be separated off in particularly pure form. The reaction temperature can be between 0° and 150° C., in the presence of proton acceptors temperatures between 20° and 80° C., and without proton acceptors between 60° and 120° C.—in particular the boiling temperature of the solvent used—being preferred. The reaction times are between 0.5 and 30 hours.

The reaction of the compounds IV with the compounds V is carried out in a similar manner to the reaction of the compounds II with the compounds III or alternatively [e.g. in the reaction of the compounds IV with compounds V in which t and v are the number 0 and R4 is the radical N(R7)R8] without additional solvent using an excess of amine as a proton acceptor and, at the same time, solvent. The reaction temperature in this case is between 60° C. and 180° C., preferably between 80° and 160° C.

The oxidation of the sulfides to the sulfoxides or sulfones is carried out under the conditions which the person skilled in the art is familiar with for the oxidation of sulfides to sulfoxides or sulfones [see for this, for example, J. Drabowicz and M. Mikolajczyk, Organic Preparations and Procedures Int. 14(1–2), 45–89 (1982) or E. Block in S. Patai, The Chemistry of Functional Groups, Supplement E. Part 1, pp. 539–608, John Wiley and Sons (Interscience Publication), 1980]. Possible oxidants are all reagents customarily used for the oxidation of sulfides to sulfoxides or sulfones.

The sulfoxides according to the invention are optically active compounds. Depending on the nature of the substituents, there can additionally be further chiral centers in the molecule. The invention therefore comprises both the enantiomers and diastereomers and their mixtures and racemates. The enantiomers can be separated in a manner known per se (for example by preparation and separation of appropriate diastereoisomeric compounds).

The starting compounds II, III, IV, and V are known or can be prepared in a manner known per se, e.g. analogously to the methods described in the following Examples.

The following Examples illustrate the invention in greater detail without restricting it. The compounds according to the invention and the starting compounds can be prepared in an analogous manner to that described in the Examples. The abbreviation RT stands for room temperature, h stands for hour(s), m.p. for melting point and dec. for decomposition.

EXAMPLES

Final Products 1. 4-(2-Furylmethylthio)-3-methyl-2-[(2-pyridinylthio)methyl]pyridine One equivalent (2.92 g) of 2-chloromethyl-4-(2-furylmethylthio)-3-methylpyridine hydrochloride (dissolved in 10 ml of water) is added dropwise at 40° C. in the course of 20 min. to a solution of 2-mercaptopyridine (1.12 g/10 mmol) in 40 ml of ethanol and 21 ml of 1 N sodium hydroxide solution. The mixture is then stirred for 2–3 h at 50–60° C. and for a further 3–4 h at RT.

The precipitated solid is filtered off with suction, washed with ethanol/water (1:1) with stirring and dried in vacuo. The title compound is obtained as an ocher-colored powder; m.p. 102–104° C.; yield: 91% of theory.

2. 4-Benzylthio-3-methyl-2-[(2-pyridinylthio)methyl]pyridine

According to the procedure described in Example 1, the title compound of m.p. 106–108° C. is obtained by reaction of 2-mercaptopyridine with 4-benzylthio-2-chloromethyl-3-methylpyridine hydrochloride.

3. 3-Methyl-4-[2-(4-methyl-5-thiazolyl)ethylthio]2-[(2-pyridinylthio)methyl]pyridine According to the procedure described in Example 1, the title compound is obtained as a yellow oil by reaction of 2-mercaptopyridine with 2-chloromethyl-4-[2-(4-methyl-5-thiazolyl)ethylthio]-3-methylpyridine hydrochloride. The product is extracted with dichloromethane, and the extract is washed with water, dried over potassium carbonate and concentrated. Crystallization from diisopropyl ether yields the title compound; m.p. 67–69° C.

4. 4-(2-Furylemthylthio)-3-methoxy-2-[(2-pyridinylthio)methyl]pyridine dihydrochloride According to the procedure indicated in Example 1, a yellow oil is obtained by reaction of 2-mercaptopyridine with 2-chloromethyl-4-(2-furylmethylthio)-3-methoxypyridine hydrochloride. The product is extracted in dichloromethane, the extract is concentrated, and the residue is dissolved in isopropanol and conc. hydrochloric acid (2.5 equivalents) is added. The mixture is concentrated again and by addition of acetone the title compound is crystallized as a colorless solid; m.p. 148° C. (dec.); yield 74% of theory.

5. 3-Methyl-4-[5-(1methyl-5-tetrazolyl)-1,5-dithiapentyl]-2-[(2-pyridinylthiomethyl]pyridine 4-(3-Chloropropylthio)-3-methyl-2-[(2-pyridinylthio)methyl]pyridine dihydrochloride(0.59 g, 1.5 mmol) is stirred at 80° C. with 5-mercapto-1-methyltetrazole (2.0 mmol) in ethanol (15 ml) for 24 h with addition of 1 N sodium hydroxide solution (5 mmol). Water is slowly added dropwise, the mixture is allowed to cool to 25° C. and the precipitated solid is filtered. After drying over $P_2O_5$, the title compound is obtained as a pale beige solid; m.p. 113–114° C.; yield 78% of theory.

6. 3-Methyl-4-[5-(4-pyridinyl)]-1,5-dithiapentyl]-2-[(2-pyridinylthio)methyl]pyridine According to the procedure indicated in Example 5, reaction of 4-(3-chloropropylthio)-3-methyl-2-[(2-pyridinylthio)methyl]pyridine dihydrochloride with 4-mercaptopyridine and sodium hydroxide solution gives the title compound; m.p. 99–102° C.; yield 67% of theory.

7. 4-[3-(4-Benzyl-1-piperazinyl)propylthio]-3-methyl-2-[(2-pyridinylthio)methyl]pyridine hydrochloride salt 4-(3-Chloropropylthio)-3-methyl-2-[(2-pyridinylthio)methyl]-pyridine dihydrochloride (0.59 g; 1.5 mmol) is stirred at 100° C. for 24 h in acetonitrile (10 ml) with benzylpiperazine (2.0 mmol) with addition of potassium carbonate (7.5 mmol) and catalytic amounts of sodium iodide. After addition of water, the mixture is extracted with dichloromethane (2×10 ml), the combined organic phases are washed with water, dried and concentrated, and the crude product (yellow oil) is chromatographed on silica gel. The pure product fractions are combined, concentrated, dissolved in ethanol and treated with 3.5 equivalents of conc. hydrochloric acid. The precipitated solid is filtered off, washed with diisopropyl ether and dried. The title compound is obtained as colorless crystals; m.p. 170–172° C.; yield 81% of theory.

8. 3-Methyl-4-[3-(4-phenyl-1-piperazinyl) propylthio]-2-[2-pyridinylthio)methyl]pyridine hydrochloride salt According to the procedure described in Example 7, reaction of 4-(3-chloropropylthio)-3-methyl-2-[(2-pyridinylthio)methyl]pyridine dihydrochloride with 1-phenylpiperazine and potassium carbonate gives the title compound; m.p. 137–140° C. (dec.); yield 46% of theory.

9. 3-Methyl-4-[3-(1,2,3.4-tetrahydroisoquinolin-2-yl)propylthio]-2-[(2-pyridinylthio)methyl]pyridine According to the procedure described in Example 7, reaction of 4-(3-chloropropylthio)-3-methyl-2-[(2-pyridinylthio)methyl]pyridine dihydrochloride with 1,2,3,4-tetrahydroisoquinoline and potassium carbonate gives the title compound; m.p. hygroscopic; dec. from 58° C.; yield 46% of theory.

10. 3-Methyl-4-{3-[4-(3-phenyl-2-propen-1-yl) piperazin-1-yl]propylthio}2-[(2-pyridinylthio) methyl]pyridine hydrochloride salt According to the procedure described in Example 7, reaction of 4-(3-chloropropylthio)-3-methyl-2-[(2-pyridinylthio)methyl]pyridine dihydrochloride with N-3-phenyl-2-propenylpiperazine gives the title compound; m.p. 205–206° C. (dec.); yield 69% of theory.

11. 4-(2-Furylmethylthio)-3-methyl-2-[(4-pyridinylthio)methyl]pyridine

According to the procedure indicated in Example 1, reaction of 4-mercaptopyridine with 2-chloromethyl-4-(2-furylmethylthio)-3-methylpyridine hydrochloride and sodium hydroxide solution, subsequent chromatography on silica gel (ethyl acetate/ethanol) and crystallization from diisopropyl ether gives the title compound as a colorless powder; m.p. 126–128° C.; yield 89% of theory.

12. 3-Methyl-4-[5-(1-methyl-5-tetrazolyl)]-1,5-dithiapentyl]-2-[(4-pyridinylthio)methyl]pyridine According to the procedure indicated in Example 5, reaction of 4-(3-chloropropylthio)-3-methyl-2-[(4-pyridinylthio)methyl]pyridine with 5-mercapto-1-methyltetrazole and sodium hydroxide solution gives the title compound as a beige powder; m.p. 95–97° C., dec., yield 59% of theory.

13. 4-[3-(4-Benzyl-1-piperazinyl)propylthio]-3-methyl -2-[(4-pyridinylthio)methyl]pyridine According to the procedure indicated in Example 7, reaction of 4-(3-chloropropylthio)-3-methyl-2-[(4-pyridinylthio)methyl]pyridine with 1-benzylpiperazine and potassium carbonate in acetonitrile, after chromatography on silica gel and crystallization of the concentrated pure fraction from diisopropyl ether, gives the title compound as a colorless solid; m.p. 79–81° C.; yield 57% of theory. A hydrated hydrochloride can be prepared from isopropanol; m.p. 165° C. (dec.); yield 87% of theory.

14. 3-Methyl-2-[(4-pyridinylthio)methyl]-4-[5-(4-pyridinyl)-1,5-dithiapentyl]pyridine According to the procedure indicated in Example 5, reaction of 4-(3-chloropropylthio)-3-methyl-2-[(4-pyridinylthio)methyl]pyridine with 4-mercaptopyridine and sodium hydroxide solution yields the title compound; m.p. 116–118° C.; Yield 69% of theory.

15. 4-[(3-Dimethyldithiocarbamoyl)propylthio]-3-methyl-2-[(4-pyridinylthio)methyl]pyridine 4-(3-Chloropropylthio)-3-methyl-2-[(4-pyridinylthio) methyl]pyridine (2 mmol) is stirred at 60° C. for 20 h with Na dimethyldithiocarbamate (2.5 mmol) in 25 ml of ethanol, the mixture is cooled and the resulting solid is filtered off. The title compound is obtained as a pale gray, crystalline powder; m.p. 112–114° C.; discoloration; yield 88% of theory.

16. 4-[3-(4-Phenyl-1-piperazinyl)propylthio]-2-[(4-pyridinylthio)methyl]pyridine According to the procedure indicated in Example 7, reaction of 4-(3-chloropropylthio)-3-methyl-2-[(4-pyridinylthio)methyl]pyridine with 1-phenylpiperazine and potassium carbonate and subsequent chromatography on silica gel gives, after crystallization from diisopropyl ether, the title compound; m.p. from 210° C. (dec.); yield 79% of theory.

17. 4-[3-(1-Imidazolyl)propylthio]-3-methyl-2-[(4-pyridinylthio)methyl]pyridine According to the procedure indicated in Example 7, reaction of 4-(3-chloropropylthio)-3-methyl-2-[(4-pyridinylthio)methyl]pyridine with imidazole (2.0 equivalents) and potassium carbonate and subsequent chromatography on silica gel (dichloromethane/acetone/NH$_3$aq) gives, after crystallization from diisopropyl ether, the title compound; m.p. 117–119° C.; yield 32% of theory.

18. 3-Methyl-4-[3-(1,2,3,4-tetrahydroisoquinolin-1-yl)propylthio]-2-[(4-pyridinylthio)methyl]pyridine According to the procedure indicated in Example 7, reaction of 4-(3-chloropropylthio)-3-methyl-2-[(4-pyridinylthio)methyl]pyridine with 1,2,3,4-tetrahydroisoquinoline, chromatography on silica gel and subsequent crystallization from isopropanol/diisopropyl ether gives the title compound; m.p. 190–192° C.; yield 36% of theory.

19. 4-{3-[4-(5-Chloro-2-thienylmethyl)-1-piperazinyl]propylthio}-3-methyl-2-[(4-pyridinylthio)methyl]pyridine trihydrochloride According to the procedure indicated in Example 7, reaction of 4-(3-chloropropylthio)-3-methyl-2-[(4-pyridinylthio)methyl]pyridine with [1-(5-chlorothiophen-2-yl)methyl]piperazine and potassium carbonate gives, after crystallization from isopropanol/acetone/conc. hydrochloric acid, the title compound; m.p. 160–162° C., dec.; yield 79% of theory.

20. 2-[[[3-Methyl-2-[(4-pyridinylthio)methyl]-4-pyridinyl]thiopropyl]thio]-1H-benzimidazole According to the procedure indicated in Example 5, reaction of 4-(3-chloropropylthio)-3-methyl-2-[(4-pyridinylthio)methyl]pyridine with 2-mercaptobenzimidazole in the presence of sodium hydroxide solution gives, after crystallization from dichloromethane/diisopropyl ether, the title compound; m.p. 128–129° C.; yield 83% of theory.

21. 4-[[5-(2-Methoxycarbonylphenyl)-1,5-dithiapent-1-yl]-3-methyl]-2-[(4-pyridinylthio)methyl]pyridine 4-(3-Chloropropylthio)-3-methyl-2-[(4-pyridinylthio)methyl]pyridine (2 mmol) is stirred in methanol (10 ml) at 25° C. for 48 h with methyl 2-mercaptobenzoate (2.2 mmol) with addition of potassium carbonate (10 mmol), the mixture is diluted with water, and the precipitated solid is filtered off and precipitated from methanol/water with stirring. After drying, the title compound is obtained as a beige powder; m.p. 85–88° C.; yield 72% of theory.

22. 3-Methyl-4-[3-(2-methyl-5-nitroimidazol-1-yl)propylthio]-2-[(4-pyridinylthio)methyl]pyridine According to the procedure indicated in Example 7, starting from 4-(3-chloropropylthio)-3-methyl-2-[(4-pyridinylthio)methyl]pyridine with 2-methyl-5-nitroimidazole, subsequent silica gel chromatography (ethyl acetate/methanol/conc. ammonia) and crystallization from diisopropyl ether gives the title compound as a yellow powder; m.p. 140–142° C.; yield 70% of theory.

23. 3-Methyl-4-(7-phenyl-1,5-dithiahept-1-yl)-2-[(4-pyridinylthio)methyl]pyridine According to the procedure indicated in Example 5, reaction of 4-(3-chloropropylthio)-3-methyl-2-[(4-pyridinylthio)methyl]pyridine with 2-phenylethyl mercaptan gives, after silica gel chromatography and crystallization from diisopropyl ether, the title compound as a colorless powder; m.p. 48–50° C.; yield 49% of theory.

24. 4-[6-(5-Chlorothiophen-2-yl)-1,5-dithiahex-1-yl]-3-methyl-2-[(4-pyridinylthio)methyl]pyridine According to the procedure indicated in Example 5, reaction of 4-(3-chloropropylthio)-3-methyl-2-[(4-pyridinylthio)methyl]pyridine with 5-chlorothiophene-2-methylmercaptan gives, after silica gel chromatography (ethyl acetate/conc. ammonia 100/1) and subsequent crystallization from diisopropyl ether, the title compound as a colorless powder; m.p. 76–77° C.; yield 58% of theory.

25. 2-{5-[3-Methyl-2-[(4-pyridinylthio)methyl]-4-pyridinyl]-1,5-dithiapentyl}pyridine-3-carboxylic acid According to the procedure indicated in Example 21, reaction of 4-(3-chloropropylthio)-3-methyl-2-[(4-pyridinylthio)methyl]pyridine with 2-mercaptonicotinic acid, and subsequent establishment of a pH of about 6 gives the title compound as a colorless solid; m.p. 219° C., dec.; yield 57% of theory.

26. 6-Methyl-4-[5-(4-pyridinyl)]-1,5-dithiapentyl]-2-[(4-pyridinylthio)methyl]pyridine sesquifumarate According to the procedure indicated in Example 5, reaction of 4-(3-chloropropylthio)-6-methyl-2-[(4-thiopyridinyl)methyl]pyridine dihydrochloride with 4-mercaptopyridine and sodium hydroxide solution gives, after chromatography of the crude product on silica gel (eluent:ethyl acetate/methanol/ammonia=40:1:1) and subsequent crystallization from acetone using 1.5 equivalents of fumaric acid, the title compound (yield 27% of theory) of m.p. 150–152° C.

27. 4-[3-(4-Benzyl-1-piperazinyl)propylthio]-6-methyl-2-[(4-pyridinylthio)methyl]pyridine difumarate According to the procedure indicated in Example 7, reaction of 4-(3-chloropropylthio)-6-methyl-2-[(4-thiopyridinyl)methyl]pyridine dihydrochloride with 1-benzylpiperazine, sodium iodide and potassium carbonate in acetonitrile gives, after chromatography of the crude product on silica gel (eluent:ethyl acetate/methanol/ammonia=19:1:1) and subsequent crystallization from acetone using 2 equivalents of fumaric acid, the title compound (yield 14% of theory) of m.p. 171–173° C.

28. 4-{3-[4-(5-Chlorothienylmethyl)-1-piperazinyl]propylthio}-6-methyl-2-[(4-pyridinylthio)methyl]pyridine difumarate According to the procedure indicated in Example 7, reaction of 4-(3-chloropropylthio)-6-methyl-2-[(4-thiopyridinyl)methyl]pyridine dihydrochloride with 1-[(5-chlorothiophen-2-yl)methyl]piperazine, sodium iodide and potassium carbonate in acetonitrile gives, after chromatography of the crude product on silica gel (eluent:ethyl acetate/methanol/ammonia=19:1:1) and subsequent crystallization from acetone using 2 equivalents of fumaric acid, the title compound (yield 38% of theory) of m.p. 148–151° C.

29. 4-[[7-(2-Methyl-5-nitroimidazol-1-yl)-1,5-dithiahept-1-yl]-3-methyl]-2-[(4-pyridinylthio)methyl]-pyridine dihydrochloride According to the procedure described in Example 5, reaction with 1-(2-mercaptoethyl)-2-methyl-5-nitroimidazole at 25° C., chromatography of the crude product on silica gel and conversion into the hydrochloride salt in acetone/hydrochloric acid gives the hygroscopic title compound; m.p. 73–78° C.; dec.; yield 39% of theory.

30. 5-{5-[3-Methyl-2-[(4-pyridinylthio)methyl]-4-pyridinyl]-1,5-dithiapent-1-yl}tetrazole-1-acetic acid The title compound is obtained according to the procedure described in Examples 25 and 21; m.p.: 185–187° C.; yield 57% of theory.

31. 4-[3-(4-Benzyl-1-pierazinyl)propylthio]-3-methyl-2-[(2-pyrimidinylthio)methyl]pyridine trihydrochloride Starting from 4-(3-chloropropylthio)-3-methyl-2-[(2-pyrimidinylthio)methyl]pyridine dihydrochloride according to the procedure described in Example 7, reaction with benzylpiperazine gives the title compound; m.p. 208° C.; decomposition; yield 49% of theory.

32. 3-Methyl-4-[3-(2-methyl-5-nitroimidazol-1-yl)propylthio]-2-[(2-pyrimidinylthio)methyl]pyridine According to the procedure described in Example 22, starting from 4-(3-chloropropylthio)-3-methyl-2-[(2-pyrimidinylthio)methyl]pyridine gives the title compound; m.p.: 141–143° C.; yield 81% of theory.

33. 3-Methyl-4-{[7-(2-methyl-5-nitroimidazol-1-yl)-1,5-dithiahept-1-yl]-3-methyl}-2-[(2-pyrimidinyl-thio)methyl]pyridine According to the procedure described in Example 5, starting from 4-(3-chloropropylthio)-3-methyl-2-[(2-pyrimidinylthio)methyl]pyridine gives the title compound as a yellow oil, which crystallizes on triturating with diethyl ether. After filtration and drying over paraffin, the title compound is obtained as a pale yellow solid; m.p. 83–85° C.; yield: 62% of theory.

Starting Compounds

A1. 4-(3-Chloropropylthio)-3-methyl-2-[(2-pyridinylthio)methyl]pyridine dihydrochloride 2-Mercaptopyridine (10 mmol) and 2-chloromethyl-4-(3-chloropropylthio)-3-methylpyridine hydrochloride (10 mmol) are heated to boiling in isopropanol (25 ml) for 4–6 h. After cooling, the precipitated solid is filtered off, washed with isopropanol and dried in vacuo at 40° C. 3.6 g (91% of theory) of the title compound are obtained as a colorless solid; m.p. 112–114° C. (dec.).

A2. 2-Chloromethyl-4-(3-chloropropylthio)-3-methylpyridine hydrochloride a) 2,3-Dimethyl-4-(3-hydroxypropylthio)pyridine-N-oxide 6 g of (60% strength) NaH are added in portions to 50 ml of dry N-methylpyrrolidone (NMP), the mixture is stirred 15 min, 9.5 g (0.11 mol) of 3-hydroxypropyl mercaptan are metered in in the course of 20 min and the mixture is stirred again for 30 min until evolution of gas has ended. A solution of 14.4 g (0.1 mol) of 4-chloro-2,3-dimethylpyridine-N-oxide in 100 ml of NMP is then added dropwise in the course of 20 min, and the reaction mixture is stirred for 1 h at RT, then for 1 h at 70° C. and after this for a further 1 h at 100° C.

After reaction has ended, the mixture is allowed to cool, and is diluted with 500 ml of water and extracted 4 times with 300 ml of dichloromethane each time. The combined organic phases are washed with water, dried over magnesium sulfate and concentrated, and the residue is crystallized from toluene. After recrystallization from methanol/toluene, the title compound is obtained as a beige solid of m.p. 106–107° C. (sublimes); yield 68% of theory.

b) 2-Hydroxymethyl-4-(3-hydroxypropylthio)-3-methylpyridine

The yellow oil obtained under a) is dissolved in 100 ml of acetic anhydride, and the mixture is stirred for 2 h at 100° C. After concentrating in vacuo, the brown, oily residue is distilled in a bulb tube distillation apparatus and reacted further without purification.

The oily distillate is heated to reflux temperature with stirring for 2 h in 100 ml of 2 N sodium hydroxide solution and 100 ml of isopropanol, isopropanol is distilled off, the residue is extracted 3 times with 100 ml of dichloromethane each time, and the combined organic phases are washed with water, dried over potassium carbonate and concentrated in vacuo. 5.0 g of 2-hydroxymethyl-4-(3-hydroxypropylthio)-3-methylpyridine are obtained, which are reacted further without purification.

A monohydrochloride of the title compound can be prepared from isopropanol using conc. hydrochloric acid; m.p. 188–190° C. (dec.).

c) 2-Chloromethyl-4-(3-chloropropylthio)-3-methylpyridine hydrochloride 5.0 g of the oil from b) are dissolved in dichloromethane (100 ml), 4 equivalents of thionyl chloride are added dropwise and the mixture is stirred at RT for 20 h. It is concentrated completely and 4.5 g of the title compound are obtained as an oily, gradually crystallizing residue. Crystallization from isopropanol/diisopropyl ether yields the title compound as a colorless solid; m.p. 142–144° C. (dec.).

A3. 4-(3-Chloropropylthio)-3-methyl-2-[(4-pyridinylthio)methyl]pyridine

According to the procedure described in Example A1., reaction of 4-mercaptopyridine with 2-chloromethyl-4-(3-chloropropylthio)-3-methylpyridine hydrochloride in isopropanol gives a hydrochloride of the title compound as a colorless solid. After dissolving in water, a pH of 10 is adjusted, the mixture is extracted 2× with dichloromethane, the organic phases are washed with sodium carbonate solution and dried (magnesium sulfate), the solvent is concentrated on a rotary evaporator and the residue is crystallized from dichloromethane/diisopropyl ether. The title compound is obtained as a colorless solid; Yield 78of theory; m.p. 88–91° C.

B1. 4-(2-Chloroethylthio)-2-chloromethyl-3-methylpyridine hydrochloride a) 2.3-Dimethyl-4-(2-hydroxyethylthio)pyridine-N-oxide According to the procedure indicated in Example A2. a), reaction of 4-chloro-2,3-dimethylpyridine-N-oxide with 2-mercaptoethanol and sodium hydride gives the title compound as an oily residue, which is employed in the subsequent step without further purification.

b) 4-(2-Hydroxyethylthio)-2-hydroxymethyl-3-methylpyridine

According to the procedure indicated in Example A2. b), reaction of the oil obtained under a) with acetic anhydride and subsequent hydrolysis with NaOH gives the title compound as an oily residue, which is employed in the subsequent step without further purification.

c) 4-(2-Chloroethylthio)-2-chloromethyl-3-methylpyridine hydrochloride

According to the procedure indicated in Example A2. c), reaction of the oil obtained under b) with thionyl chloride gives the title compound as an oily residue which is employed directly as a solution in ethanol for the reaction with 2-mercaptobenzimidazole.

C1. 2-Chloromethyl-4-(3-chloropropylthio)-3-methoxypyridine hydrochloride

According to the procedure described in Example A2. a)–c), starting from 4-chloro-3-methoxy-2-methylpyridine, reaction first with 3-hydroxypropyl mercaptan, then successively with acetic anhydride, sodium hydroxide solution and thionyl chloride, gives the title compound as a yellow, slowly crystallizing oil, which is used directly for the reaction with mercaptopyridines.

D1. 3-Chloro-4-[N-(2-chloroethyl)-N-methylamino]-2-[(2-pyridinylthio)methyl]pyridine dihydrochloride According to the procedure described in Example A1., reaction of 3-chloro-4-[N-(2-chloroethyl)N-methylamino]-2-chloromethyl hydrochloride with 4-mercaptopyridine (1 equivalent) in isopropanol gives the title compound as a colorless solid; m.p. 208–210° C., dec. (Yield 81% of theory).

D2. 3-Chloro-4-[N-(2-chloroethyl)-N-methylamino]-2-chloromethylpyridine hydrochloride a) 3-Chloro-4-[N-(2-hydroxyethyl)-N-methylamino]-2-hydroxymethylpyridine A mixture of 3,4-dichloro-2-hydroxymethylpyridine (J. Med. Chem. 1989, 32, 1970) (2.5 g) in 2-methylaminoethanol (30 ml) is heated at 160° C. for 2.5 h in a steel autoclave, the excess amine is stripped off in a high vacuum and the residue which remains is chromatographed on silica gel (dichloromethane/methanol 95/5). Yield: 2.3 g as a yellowish oil.

b) 3-Chloro-4-[N-(2-chloroethyl)-N-methylamino]-2-chloromethylpyridine hydrochloride A solution of 3-chloro-4-[N-(2-hydroxyethyl)-N-methylamino]-2-hydroxymethylpyridine (2.3 g) in dichloromethane (30 ml) is treated dropwise at 0° C. with a solution of thionyl chloride (4 ml) in dichloromethane (20 ml). The temperature is then allowed to climb to 20° C. (20 min) and the temperature is then kept at 400° C. for 30 min. After stripping off the solvent in vacuo, the residue which remains is chromatographed on silica gel (petroleum ether/ethyl acetate 7/3 mixture which contains 1 ml of conc. $NH_3 \times aq/L$). Yield: 2.6 g.

E1. 4-(3-Chloropropylthio)-6-methyl-2-[(4-thiopyridinyl)methyl]pyridine dihydrochloride 4-Mercaptopyridine (10.9 mmol) and 2-chloromethyl-4-(3-chloropropylthio)-6-methylpyridine hydrochloride (10.9 mmol) are heated to boiling for 6 h in isopropanol (25 ml). After cooling to RT, methanol (25 ml) and silica gel (10 g) are added, the mixture is concentrated to dryness and the residue is then chromatographed on silica gel (eluent:ethyl acetate/methanol/ammonia=19:1:1). The fractions of $R_f$=0.3 are concentrated, dissolved in a little acetone and treated with 2 equivalents of conc. hydrochloric acid. The precipitate is filtered off with suction and dried in a high vacuum. 3.55 g (82% of theory) of the title compound are obtained as a beige solid; m.p. 194–1970° C.

E2. 2-Chloromethyl-4-(3-chloropropylthio)-6-methylpyridine hydrochloride a) 2,6-Dimethyl-4-(3-hydroxypropylthio)pyridine-N-oxide 12 g of (60% strength) NaH are added in portions to 50 ml of dry N-methylpyrrolidone (NMP). The mixture is stirred for 10 min. 19 g (0.22 mol) of 3-hydroxypropyl mercaptan are metered in the course of 30 min and the mixture is stirred for a further 30 min until evolution of gas has ended. A solution of 28.8 g (0.2 mol) of 4-chloro-2,6-dimethylpyridine-N-oxide in 150 ml of NMP is then added dropwise in the course of 30 min, and the reaction mixture is stirred for 1 h at RT, then for 1 h at 70° C. and after this for a further 1 h at 100° C.

After reaction has ended the mixture is allowed to cool, and is diluted with 700 ml of water and extracted first 4 times with 300 ml of dichloromethane each time and then a further 4 times with 300 ml of dichloromethane/n-butanol (10:1) each time. The combined organic extracts are dried over magnesium sulfate and concentrated and the residue is crystallized from toluene. The title compound is isolated as a beige solid of m.p. 117–119° C. Yield 59% of theory.

b) 2-Hydroxymethyl-4-(3-hydroxypropylthio)-6-methylpyridine

The product obtained under a) is dissolved in 100 ml of acetic anhydride and the solution is stirred at 100° C. for 2 h. After concentrating in vacuo, the brown, oily residue is distilled in a bulb tube distillation apparatus and reacted further without purification.

The oily distillate is heated at reflux for 2 h with 100 ml of 2 N sodium hydroxide solution and 100 ml of isopropanol. Isopropanol is distilled off and the residue is extracted 4 times with 100 ml of dichloromethane each time and 4 times with 100 ml of dichloromethane/n-butanol (10:1) each time. The combined organic extracts are washed with water, dried over potassium carbonate and concentrated in vacuo. 4.2 g of the title compound are obtained as an oil, which is reacted further without purification.

After chromatography on silica gel (eluent:ethyl acetate/methanol=10:1) and subsequent crystallization from diisopropyl ether, the title compound is isolated in crystalline form. M.p. 94–96° C.

c) 2-Chloromethyl-4-(3-chloropropylthio)-6-methylpyridine hydrochloride 4.0 g of the oil from b) are dissolved in dichloromethane (80 ml), 4 equivalents of thionyl chloride are added dropwise and the mixture is stirred at RT for 48 h. 20 ml of toluene are added, the mixture is concentrated completely, the residue is dried in a high vacuum and 5.3 g of the title compound are obtained as a yellow oil. 1H-NMR(DMSO-DMSO-D6, delta ppm); 7.88 (d,1H), 7.77 (d,1H), 5.00 (s,2H), 3.79 (t,2H), 3.40 (t,2H), 2.70 (s,3H), 2.14 (m,2H).

F1. 4-(3-Chloropropylthio)-3-methyl-2-[(2-pyrimidinylthio)methyl]pyridine

According to the procedure described in Example A3., reaction with 2-mercaptopyrimidine gives the title compound; m.p. 83–85° C.; colorless powder; yield 73% of theory.

COMMERCIAL UTILITY

The excellent activity of compounds of the formula I and their salts against Helicobacter bacteria permits their use in human medicine as active compounds for the treatment of diseases which are based on Helicobacter bacteria.

The invention therefore further relates to a method for the treatment of mammals, in particular humans, who are suffering from diseases which are based on Helicobacter bacteria. The method comprises administering to the sick individual a therapeutically efficacious and pharmacologically tolerable amount of one or more compounds of the formula I and/or their pharmacologically tolerable salts.

The invention additionally relates to the compounds of the formula I and their pharmacologically tolerable salts for use in the treatment of diseases which are based on Helicobacter bacteria.

The invention likewise comprises the use of compounds of the formula I and their pharmacologically tolerable salts in the production of medicaments which are employed for the control of those diseases which are based on Helicobacter bacteria.

The invention further relates to medicaments for the control of Helicobacter bacteria, which contain one or more compounds of the general formula I and/or their pharmacologically tolerable salts.

Of the Helicobacter strains against which the compounds of the formula I prove to be effective, the strain Helicobacter pylori may be mentioned in particular.

The medicaments are prepared by processes which are known per se and with which the person skilled in the art is familiar. As medicaments, the pharmacologically active compounds of the formula I and their salts (=active compounds) are employed either as such, or preferably in combination with suitable pharmaceutical auxiliaries, e.g. in the form of tablets, coated tablets, capsules, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Besides solvents, gel-forming agents, tablet auxiliaries and other active compound excipients, for example, antioxidants, dispersants, emulsifiers, antifoams, flavor corrigents, preservatives, solubilizers, colorants or permeation promoters and complexing agents (e.g. cyclodextrins) can be used.

The active compounds can be administered, for example, parenterally (e.g. intravenously) or, in particular, orally.

In general, in human medicine the active compounds are administered in a daily dose of approximately 0.2 to 50, preferably 1 to 30, mg/kg of body weight, if appropriate in the form of several, preferably 2 to 6, individual doses to achieve the desired result.

In this connection, it is particularly to be mentioned as an essential aspect of the invention that the compounds of the formula I in which n is the number 0 even prove effective against Helicobacter bacteria on administration of those doses which are below the doses which had to be employed to achieve an inhibition of gastric acid secretion sufficing for therapeutic purposes.

Compounds of the formula I in which n is the number 1 also have—besides their activity against Helicobacter bacteria—a marked gastric acid secretion-inhibiting action. Accordingly, these compounds can also be employed for the treatment of those diseases which are based on increased gastric acid secretion.

The compounds according to the invention can also be administered in a fixed or free combination together with a substance neutralizing gastric acid and/or inhibiting gastric acid secretion and/or with a substance suitable for the classical control of Helicobacter pylori.

Substances neutralizing gastric acid which may be mentioned are, for example, sodium hydrogen carbonate or other antacids (such as aluminum hydroxide, magnesium aluminate or magaldrate). Gastric acid secretion-inhibiting substances which may be mentioned are, for example, $H_2$ blockers (e.g. cimetidine, ranitidine), $H^+/K^+$ ATPase inhibitors (e.g. lansoprazole, omeprazole or, in particular, pantoprazole) and also so-called peripheral anticholinergics (e.g. pirenzepine, telenzepine).

Substances suitable for the classical control of Helicobacter pylori which may be mentioned are, in particular, substances having antimicrobial activity such as, for example, penicillin G, gentamycin, erythromycin, nitrofurazone, tinidazole, nitrofurantoin, furazolidone, metronidazole and in particular amoxycillin, or else bismuth salts such as, for example, bismuth citrate.

Biological Investigations

The compounds of the formula I were investigated for their activity against Helicobacter pylori following the methodology described by Tomoyuki Iwahi et al. (Antimicrobial Agents and Chemotherapy, 1991, 490–496) using Columbia agar (Oxoid) and with a growth period of 4 days. For the compounds investigated, the approximate MIC 50 values listed in Table A which follows resulted here (the numbers of the compounds indicated correspond to the example numbers in the description).

TABLE A

| Compound No. | Approx. MIC 50 (μg/ml) |
| --- | --- |
| 3 | ≦0,5 |
| 6 | ≦0,5 |
| 11 | ≦0,5 |
| 14 | ≦0,5 |
| 15 | ≦0,5 |
| 16 | ≦0,5 |
| 29 | ≦0,5 |
| 32 | ≦0,5 |

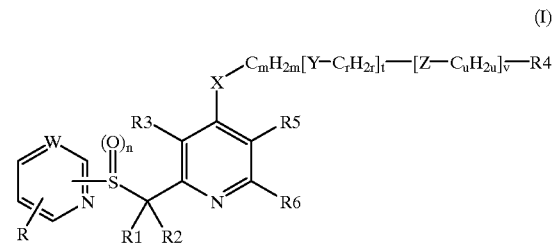

(I)

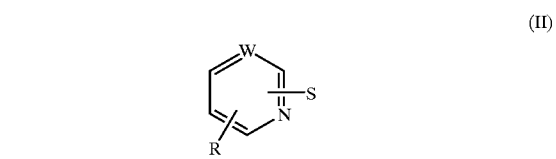

(II)

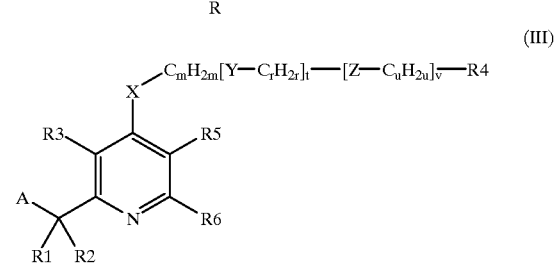

(III)

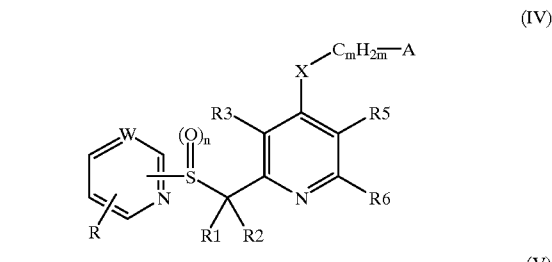

(IV)

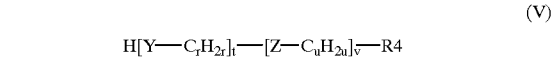

(V)

What is claimed is:
1. A compound of the formula I

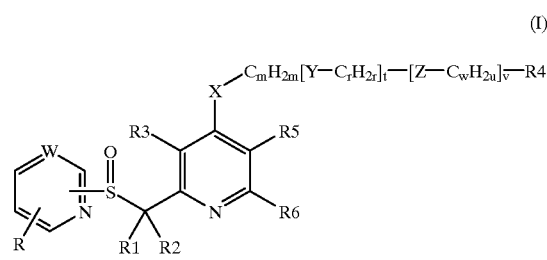

(I)

33 in which

R is hydrogen, 1–4C-alkyl, halogen, trifluoromethyl, 1–4C-alkoxycarbonyl, carboxyl or cyano, R1 is hydrogen or 1–4C-alkyl, R2 is hydrogen or 1–4C-alkyl, R3 is hydrogen, 1–4C-alkyl, 1–4C-alkoxy or halogen, R4 is a mono- or di-1–4C-alkylcarbamoyl or -thiocarbamoyl radical, an N-1–4C-alkyl-N'-cyanoamidino radical, a 1-N-1–4C-alkylamino-2-nitroethylene radical, an N-2-propynyl-N'-cyanoamidino radical, an aminosulfonylamidino radical, the radical —N(R7)R8 or an R9- and R10-substituted cyclic system or bicyclic system which is selected from the group consisting of benzene, naphthalene, furan, thiophene, pyrrole, oxazole, isoxazole, thiazole, thiazoline, isothiazole, imidazole, imidazoline, pyrazole, triazole, tetrazole, thiadiazole, thiadiazole-1-oxide, oxadiazole, pyridine, pyridine-N-oxide, pyrimidine, triazine, pyridone, benzimidazole, imidazopyridine, benzothiazole, benzoxazole and quinoline, R5 is hydrogen, 1–4C-alkyl, 1–4C-alkoxy or halogen, R6 is hydrogen or 1–4C-alkyl, R7 is 1–7C-alkyl, 3–7C-cycloalkyl or Ar-1–4C-alkyl and R8 is 1–7C-alkyl, 3–7C-cycloalkyl or Ar-1–4C-alkyl, where Ar is phenyl, furyl, naphthyl, tetrahydronaphthyl or R11-, R12- and R13-substituted phenyl, or in which R7 and R8 together, and including the nitrogen atom to which both are bonded, are an unsubstituted or substituted 5- or 6-membered ring hetero(bi)cyclic system, which is selected from the group consisting of piperidine, piperazine, morpholine, indoline, 1,2,3,4-tetrahydroquinoline and 1,2,3,4-tetrahydroisoquinoline, where a substituted piperidino radical is substituted by one, two or three identical or different substituents selected from the group consisting of 1–4C-alkyl, 1–4C-alkoxycarbonyl, hydroxy-1–4C-alkyl, phenyl, R11-, R12- and R13-substituted phenyl, phenyl-1–4C-alkyl, benzoyl, halogen-substituted benzoyl and carboxyl, a substituted piperazino radical can be substituted in the 2-, 3-, 5- or 6-position by a 1–4C-alkyl radical and is substituted in the 4-position by a substituent selected from the group consisting of 1–4C-alkyl, 3–7C-cycloalkyl, 3–7C-cycloalkyl-1–4C-alkyl, 1–4C-alkoxycarbonyl-1–4C-alkyl, carbamoyl, —$C_pH_{(2p-2)}$—R14 and —$C_qH_{2q}$—R14, a substituted morpholino radical is substituted by one or two identical or different 1–4C-alkyl radicals, a substituted indolin-1-yl radical, substituted in the 2- and/or 3-position by a carboxyl group or by one or two identical or different 1–4C-alkyl radicals, or substituted in the benzo moiety by one or two identical or different substituents selected from the group consisting of 1–4C-alkyl, halogen and nitro, a substituted 1,2,3,4-tetrahydroquinoline radical is substituted by one or two identical or different substituents selected from the group consisting of 1–4C-alkyl and halogen, a substituted 1,2,3,4-tetrahydroisoquinoline radical is substituted by one or two identical or different substituents selected from the group consisting of 1–4C-alkyl, carboxyl and phenyl,

34

R9 is hydrogen, 1–4C-alkyl, hydroxyl, 1–4C-alkoxy, halogen, nitro, guanidino, carboxyl, 1–4C-alkoxycarbonyl, R15-substituted 1–4C-alkyl or —N(R16)R17, R10 is hydrogen, 1–4C-alkyl, hydroxyl, 1–4C-alkoxy, halogen or trifluoromethyl, R11 is hydrogen, 1–4C-alkyl, hydroxyl 1–4C-alkoxy, 1–4C-alkylcarbonyl, halogen, 1–4C-alkylamino or nitro, R12 is hydrogen, 1–4C-alkyl, hydroxyl, 1–4C-alkoxy, halogen or nitro, and R13 is hydrogen or trifluoromethyl, R14 is an R9- and R10-substituted cyclic system or bicyclic system which is selected from the group consisting of benzene, naphthalene, furan, thiophene, pyrrole, oxazole, isoxazole, thiazole, thiazoline, isothiazole, imidazole, imidazoline, pyrazole, triazole, tetrazole, thiadiazole, oxadiazole, pyridine, pyridine-N-oxide, pyrimidine, benzimidazole and quinoline, R15 is hydroxyl, 1–4C-alkoxy, carboxyl, 1–4C-alkoxycarbonyl or —N(R16)R17, where R16 is hydrogen, 1–4C-alkyl or —CO—R18 and R17 is hydrogen or 1–4C-alkyl, or where R16 and R17, together and including the nitrogen atom to which both are bonded, are a piperidino or morpholino radical, R18 is hydrogen, 1–4C-alkyl or 1–4C-alkoxy, W is CH or N, X is O (oxygen), N-1–4C-alkyl or S, Y is O (oxygen), N-1–4C-alkyl, S, SO or $SO_2$, Z is O (oxygen), N-1–4C-alkyl, S, SO or $SO_2$, m is a number from 1 to 7, n is the number 0, 1 or 2, r is a number from 2 to 4, t is the number 0 or 1, u is a number from 0 to 4, v is the number 0 or 1, p is a number from 2 to 4 and q is a number from 0 to 4 or a salt thereof, where t and/or v are not the number 1 if m is the number 1,

Z is not SO or $SO_2$ if u is the number 0, and where

R4 is not —N(R7)R8 or an N (nitrogen)-bonded cyclic system or bicyclic system if Z is O, S, SO or $SO_2$, v is the number 1 and u is the number 0.

2. A compound of the formula I as claimed in claim 1, in which

R is hydrogen or 1–4C-alkyl,

R1 is hydrogen,

R2 is hydrogen,

R3 is hydrogen, 1–4C-alkyl, 1–4C-alkoxy or halogen,

R4 is a mono- or di-1–4C-alkylthiocarbamoyl radical, the radical —N(R7)R8 or an R9- and R10-substituted cyclic system or bicyclic system which is selected from the group consisting of benzene, furan, thiophene, thiazole, isothiazole, imidazole, triazole, tetrazole, thiadiazole, pyridine, pyrimidine, benzimidazole and quinoline, R5 is hydrogen R6 is hydrogen or 1–4C-alkyl, R7 is 1–7C-alkyl and R8 is Ar-1–4C-alkyl, where Ar is phenyl, or in which R7 and R8, together and including the nitrogen atom to which both are bonded, are an unsubstituted or substituted 5- or 6-membered ring hetero(bi)cyclic system which is selected from the group consisting of piperidine, piperazine and 1,2,3,4-tetrahydroisoquinoline, where
  a substituted piperidino radical is substituted by one, two or three identical or different substituents selected from the group consisting of 1–4C-alkyl, phenyl and phenyl-1–4C-alkyl,
  a substituted piperazino radical is substituted in the 4-position by a substituent selected from the group consisting of 1–4C-alkyl, 1–4C-alkoxycarbonyl-1–4C-alkyl, —$C_pH_{(2p-2)}$—R14 and —$C_qH_{2q}$—R14,
  a substituted 1,2,3,4-tetrahydroisoquinoline radical is substituted by one or two identical or different substituents selected from the group consisting of 1–4C-alkyl and carboxyl, R9 is hydrogen, 1–4C-alkyl, halogen, nitro, carboxyl, 1–4C-alkoxycarbonyl or R15-substituted 1–4C-alkyl, R10 is hydrogen or 1–4C-alkyl, R14 is an R9- and R10-substituted cyclic system or bicyclic system which is selected from the group consisting of benzene, furan, thiophene, thiazole, isothiazole, imidazole, triazole, tetrazole, thiadiazole, pyridine, pyrimidine, benzimidazole and quinoline, R15 is carboxyl, 1–4C-alkoxycarbonyl or —N(R16)R17, where
  R16 is 1–4C-alkyl and
  R17 is 1–4C-alkyl, or where
  R16 and R17, together and including the nitrogen atom to which both are bonded, are a piperidino or morpholino radical, W is CH or N, X is S, Z is S, m is a number from 1 to 5, n is the number 0, t is the number 0, u is a number from 0 to 2, v is the number 0 or 1, p is a number from 2 to 4 and q is a number from 0 to 2 or a salt thereof, where v is not the number 1 if m is the number 1, and where

R4 is not —N(R7)R8 or an N (nitrogen)-bonded cyclic system or bicyclic system if Z is S, v is the number 1 and u is the number 0.

3. A compound of the formula I as claimed in claim 1, in which
  R is hydrogen,
  R1 is hydrogen,
  R2 is hydrogen,
  R3 is hydrogen, 1–4C-alkyl or 1–4C-alkoxy,
  R4 is a di-1–4C-alkylthiocarbamoyl radical, the radical —N(R7)R8 or an R9- and R10-substituted cyclic system or bicyclic system which is selected from the group consisting of benzene, furan, thiophene, thiazole, imidazole, tetrazole, pyridine and benzimidazole,
  R5 is hydrogen,
  R6 is hydrogen or 1–4C-alkyl,
  R7 and R8, together and including the nitrogen atom to which both are bonded, are an unsubstituted or substituted piperazino radical or a 1,2,3,4-tetrahydroisoquinoline radical, where
    a substituted piperazino radical is substituted by a substituent selected from the group consisting of —$C_pH_{2p-2)}$—R14 and —$C_qH_{2q}$—R14,
  R9 is hydrogen, 1–4C-alkyl, halogen, nitro, carboxyl, 1–4C-alkoxycarbonyl or R15-substituted 1–4C-alkyl,
  R10 is hydrogen or 1–4C-alkyl,
  R14 is an R9- and R10-substituted cyclic system which is selected from the group consisting of benzene and thiophene,
  R15 is carboxyl,
  W is CH or N,
  X is S,
  Z is S,
  m is a number from 1 to 3,
  n is the number 0,
  t is the number 0,
  u is the number 0, 1 or 2,
  v is the number 0 or 1,
  p is the number 3 and
  q is the number 0 or 1
  or a salt thereof, where
  v is not the number 1 if m is the number 1, and where
  R4 is not —N(R7)R8 or an N (nitrogen)-bonded cyclic system or bicyclic system if Z is S, v is the number 1 and u is the number 0.

4. A compound of the formula I as claimed in claim 1, in which t is the number 0 and v is the number 0, or a salt thereof.

5. A compound of the formula I as claimed in claim 1, in which t is the number 0, v is the number 1 and u is the number 0, or a salt thereof.

6. A compound of the formula I as claimed in claim 1, in which t is the number 0, v is the number 1 and u is the number 1 or 2, or a salt thereof.

7. A compound of the formula I as claimed in claim 1, in which the pyridine or pyrimidine ring is bonded in the 2-position.

8. A compound of the formula I as claimed in claim 1, in which the pyridine or pyrimidine ring is bonded in the 4-position.

9. A compound of claim 1 wherein W is CH.

10. A compound of claim 1 wherein W is N.

11. A process for preparing a compound of formula I as claimed in claim 1 or a salt thereof, which comprises:
  reacting a mercapto compound of formula II

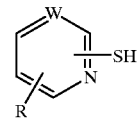

(II)

in which R and W have a meaning specified in claim 1, with a pyridine derivative III

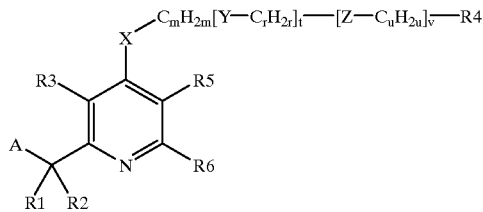

(III)

in which R1, R2, R3, R4, R5, R6, X, Y, Z, m, r, t, u and v have a meaning specified in claim 1, and A is a suitable leaving group, and, optionally, converting an obtained compound into a corresponding salt or converting an obtained salt into a corresponding free compound.

12. A process of claim 11 wherein W is CH.

13. In a method of controlling Helicobacter bacteria which comprises contacting such bacteria with an effective amount of a suitable compound, the improvement wherein the suitable compound is a compound of claim 1 or a salt thereof.

14. In a process which comprises administering an effective amount of a suitable pharmacologically-active compound to a mammal suffering from a disease based on Helicobacter bacteria, the improvement wherein the compound is a compound of claim 1 or a salt thereof.

15. In a process for preparing a medicament composition having an effective amount of active ingredient for treating a disease based on Helicobacter bacteria and a suitable carrier, the improvement wherein the active ingredient is a compound of claim 1 or a pharmacologically tolerable salt thereof.

16. In a medicament composition having an effective amount of an active ingredient for treating a disease based on Helicobacter bacteria and a suitable pharmaceutical auxiliary, the improvement wherein the active ingredient is a compound of claim 1 or a pharmacologically tolerable salt thereof.

17. A method of claim 13 wherein W is CH.

18. A process of claim 14 wherein W is CH.

19. A process of claim 15 wherein W is CH.

20. A composition of claim 16 wherein W is CH.

* * * * *

UNITED STATES PATENT AND TRADEMARK OFFICE
CERTIFICATE OF CORRECTION

| | |
|---|---|
| PATENT NO. | : 6,162,809 |
| DATED | : December 19, 2000 |
| INVENTOR(S) | : Bernhard Kohl et al. |

It is certified that error appears in the above-identified patent and that said Letters Patent is hereby corrected as shown below:

<u>Title page,</u>
Item [86], "Jan. 17, 1995" should read -- Jan.17, 1997 --;
Item [30], "Jul. 10, 1994" should read -- Jul. 20, 1994 --.

Signed and Sealed this

Second Day of October, 2001

Attest:

NICHOLAS P. GODICI
*Attesting Officer*    *Acting Director of the United States Patent and Trademark Office*